US011931475B1

(12) United States Patent
Musco

(10) Patent No.: US 11,931,475 B1
(45) Date of Patent: Mar. 19, 2024

(54) AUTOMATIC AIR CONDITIONER DRAIN SYSTEM SANITIZER

(71) Applicant: Richard G. Musco, Lake Worth, FL (US)

(72) Inventor: Richard G. Musco, Lake Worth, FL (US)

( * ) Notice: Subject to any disclaimer, the term of this patent is extended or adjusted under 35 U.S.C. 154(b) by 0 days.

(21) Appl. No.: 18/199,936

(22) Filed: May 20, 2023

Related U.S. Application Data

(63) Continuation-in-part of application No. 17/962,622, filed on Oct. 10, 2022, now Pat. No. 11,696,965.

(51) Int. Cl.
*A61L 2/18* (2006.01)
*A61L 2/26* (2006.01)
*F24F 13/22* (2006.01)

(52) U.S. Cl.
CPC .............. *A61L 2/18* (2013.01); *A61L 2/26* (2013.01); *F24F 13/222* (2013.01); *A61L 2202/14* (2013.01); *A61L 2202/15* (2013.01); *F24F 2221/225* (2013.01)

(58) Field of Classification Search
CPC .......... A61L 2/18; A61L 2/26; A61L 2202/14; A61L 2202/15; F24F 13/222; F24F 2221/225
See application file for complete search history.

(56) References Cited

U.S. PATENT DOCUMENTS

| 5,514,344 | A | * | 5/1996 | D'Agaro | ................... A61L 2/18 137/561 A |
|---|---|---|---|---|---|
| 5,558,158 | A | | 9/1996 | Elmore | |
| 5,755,103 | A | | 9/1998 | Na et al. | |
| 6,487,868 | B2 | | 12/2002 | Sato et al. | |
| 7,278,272 | B2 | | 10/2007 | Huston et al. | |
| 8,057,751 | B2 | | 11/2011 | Cheong et al. | |
| 9,943,778 | B1 | | 4/2018 | Gutierrez et al. | |
| 10,139,119 | B2 | | 11/2018 | Choi et al. | |
| 10,220,220 | B2 | | 3/2019 | Kim et al. | |
| 10,928,083 | B2 | | 2/2021 | Park et al. | |

\* cited by examiner

*Primary Examiner* — Sean E Conley
(74) *Attorney, Agent, or Firm* — Cramer Patent & Design PLLC; Aaron R. Cramer

(57) ABSTRACT

Embodiments of the present disclosure may include an automatic air conditioner drain system sanitizer, including a pump moving a plurality of drain sanitizer solution from a pump inlet to a pump outlet automatically. Embodiments may also include a solution reservoir containing a drain sanitizer solution. In some embodiments, the solution reservoir includes a solution reservoir lid, an atmospheric equalization vent, and a solution reservoir tubing coupler. In some embodiments, the pump draws the drain sanitizer solution into the pump from the solution reservoir. Embodiments may also include a pump controller circuit board which operates the pump. Embodiments may also include a wireless communications circuit board which provides control, settings adjustments, system dispensing history data and system overall health status.

20 Claims, 26 Drawing Sheets

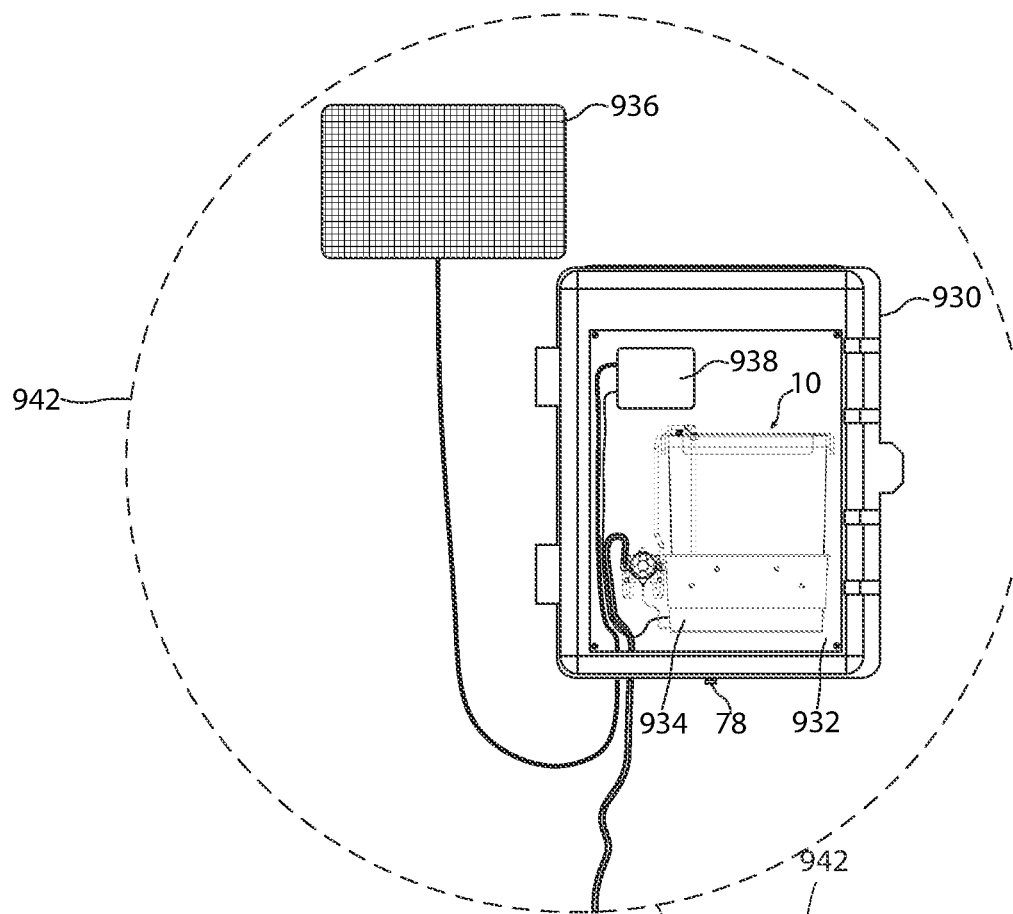
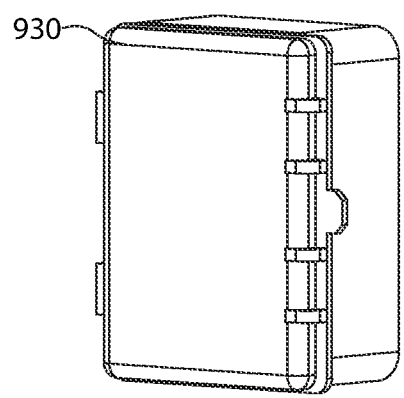
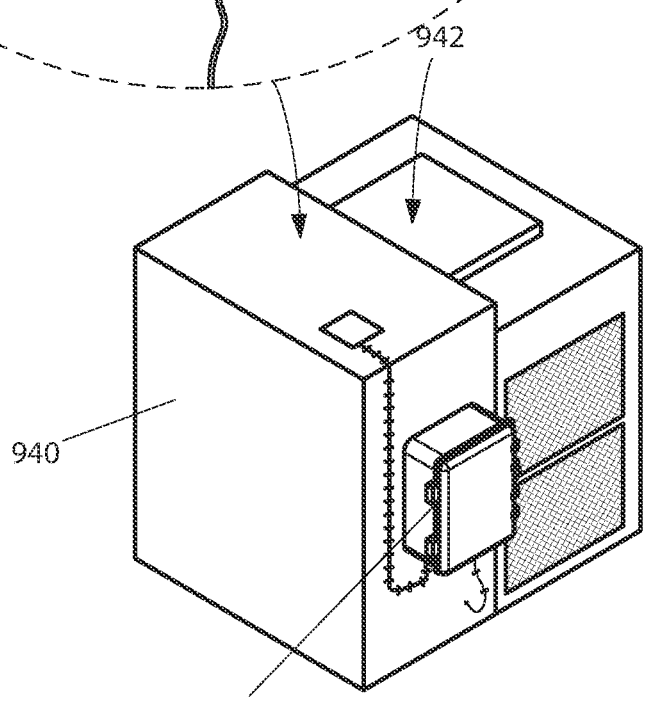

AUTOMATIC AIR CONDITIONER DRAIN SYSTEM SANITIZER

RELATED APPLICATIONS

The present invention was first described in and is a continuation in part of U.S. Utility application Ser. No. 17/962,622 filed Oct. 10, 2022, the entire disclosures of which are incorporated herein by reference.

FIELD OF THE INVENTION

The present invention relates generally to a drain sanitizer system and more specifically to an automatic drain sanitizing system for an air conditioner.

BACKGROUND OF THE INVENTION

The recent advancements in air conditioning have greatly enhanced the quality of human life. Some even argue that air conditioning is a more significant invention for mankind than the computer. However, despite the numerous benefits of air conditioning, the process of producing a negative heat delta presents various challenges. One major difficulty relates to the accumulation and disposal of condensate, which is formed on the cold surfaces of the air conditioning evaporator coil. The condensate drain system begins at the evaporator's condensate collection drain pan and ends at the final discharge location of the drain line system. Unfortunately, the combination of damp and warm conditions within the air conditioner, along with airborne biological matter, creates an ideal environment for the growth of bacteria.

Scientifically known as "Zoogloea," this bacteria are commonly referred to as "white slime" due to its gelatinous and slimy consistency. If left untreated, Zoogloea multiplies to the extent that it completely clogs the drain system, preventing the proper discharge of condensate. As a result, the blockage causes the condensate to back up all the way to the evaporator's condensate collection drain pan. Air conditioning systems equipped with a condensate backup detection switch will shut off when a backup occurs. However, if the backup goes unnoticed or persists for an extended period during hot and humid weather, it can lead to the rapid growth of mold on interior surfaces. This mold problem becomes even more severe when a residence or business remains vacant for a prolonged time, requiring extensive mold remediation efforts. If the air conditioner lacks a backup detection switch, condensate generation continues unabated until the issue is discovered, leading to overflow in the evaporator's condensate collection drain pan. This continuous overflow can cause significant water damage to properties located near or below the air conditioning system, along with additional health risks associated with the breeding of hidden mold and mildew. The estimated annual cost of damage caused by backed-up condensate drain lines exceeds one billion dollars.

Compounding the issue of extensive bacterial growth is the shift in evaporator manufacturing construction from copper tubing to aluminum tubing. Copper tubing and fittings possess some antibacterial properties due to the generation of copper ions when condensate comes into contact with copper. These ions help minimize bacterial growth. However, as Original Equipment Manufacturers (OEMs) transition to aluminum tubing in evaporator coil systems to cut costs, the bacterial production within the evaporator system is expected to increase, as observed in the industry. Consequently, there is an urgent need for a robust, practical, and cost-effective solution to eliminate bacterial growth in condensate collection and drain systems automatically and continuously. The development of an automatic air conditioner drain line sanitizer addresses this critical requirement in a manner which is novel and cost effective.

SUMMARY OF THE INVENTION

Embodiments of the present disclosure may include an automatic air conditioner drain system sanitizer, including a pump moving a plurality of drain sanitizer solution from a pump inlet to a pump outlet automatically. Embodiments may also include a solution reservoir containing a drain sanitizer solution. In some embodiments, the solution reservoir includes a solution reservoir lid, an atmospheric equalization vent, and a solution reservoir tubing coupler.

In some embodiments, the pump draws the drain sanitizer solution into the pump from the solution reservoir. Embodiments may also include a pump controller circuit board which operates the pump. Embodiments may also include a wireless communications circuit board which provides control, settings adjustments, system dispensing history data and system overall health status. Embodiments may also include an operator interface momentary pushbutton switch which enables a plurality of utilities including, but not limited to, manual continuous pump activation control, selection of pre-set quantity pump dispense controls, incoming power level indication, dispense interval frequency selection control and dispense quantity timing selection control.

In some embodiments, the pump may be an electromechanical pump. In some embodiments, the pump may be a peristaltic pump. In some embodiments, the pump moves the drain sanitizer solution by applying a rotary motion, a reciprocating motion, a linear motion, or a combination thereof by one or more gears, one or more screws, one or more pistons, one or more rollers, one or more shuttle blocks, one or more vanes, one or more diaphragms, one or more plungers, one or more impellers or combinations thereof.

In some embodiments, the pump draws the drain sanitizer solution into the pump from the solution reservoir through a plurality of intake tubing that may be coupled via fluid communication to the pump inlet via an intake tubing coupler. In some embodiments, the pump discharges the drain sanitizer solution through a plurality of discharge tubing that may be coupled via fluid communication to the pump outlet via a discharge tubing coupler.

In some embodiments, the drain sanitizer solution may be dispensed through the discharge tubing into a condensate collection and removal drain system. In some embodiments, the drain line may be operable to drain a plurality of condensation from an evaporator. In some embodiments, the drain sanitizer solution kills a plurality of microorganisms in a condensate collection and removal drain system pathway to prevent clogging.

In some embodiments, the discharge tubing may be routed into a bottom of the evaporator via an accessory drain port plug which may be fitted with a pass-through bulkhead tubing coupler. In some embodiments, the discharge tubing may be routed into a drain pan under an evaporator which may be coupled via fluid communication to the drain line. In some embodiments, the discharge tubing may be routed into a bottom of a evaporator via a pass-through bulkhead tubing coupler fitted to an added aperture in the evaporator housing access panel.

In some embodiments, the discharge tubing may be routed directly into the drain line via a condensate drain line vent tube. Embodiments may also include a cap may be replaced with a different cap which may be fitted with a pass-through bulkhead tubing coupler and a venting aperture. In some embodiments, the discharge tubing may be routed into the drain line via a condensate drain line access port that may be closed with a cap.

In some embodiments, the cap may be replaced with a different cap which may be fitted with a pass-through bulkhead tubing coupler. In some embodiments, the controller may be a microcontroller having a computer processor that includes a central processing unit having one or more integrated circuits that determines when to dispense the drain sanitizer solution, when to energize the pump, which direction to rotate the pump, when to control the drain sanitizer solution dispensed and when to deenergize a motor.

Embodiments may also include a timer counts a plurality of clock ticks in order to track elapsed time. In some embodiments, the controller receives one or more inputs from an internal timer and controls one or more outputs coupled to a motor drive circuit. In some embodiments, the controller includes a battery pack containing one or more batteries.

In some embodiments, the automatic air conditioner drain system sanitizer, according to may include a liquid pumping system housing which incorporates the pump controller circuit board, wireless communication circuit board, dispensing pump, input DC power connector and a pushbutton switch with a LED indicator light. Embodiments may also include a plurality of circular mounting magnets may be coupled to a rear face of a component mounting fixture. The component mounting fixture efficiently organizes the mounting of the sanitizing solution reservoir, liquid pumping system and an optional battery pack. The liquid pumping system housing may include a single circular mounting magnet coupled to the rear face of the housing depending on the application.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

FIG. 23*a* is an in-use view of an automatic air conditioner drain system sanitizer 10, according to a method of use of the present invention, illustrating an example of an outdoor installation on a commercial roof-mounted air conditioning system 940;

FIG. 23*b* is an orthogonal view of an automatic air conditioner drain system sanitizer 10, according to a method of use of the present invention, illustrating a waterproof enclosure 930;

FIG. 23*c* is a close-up view of an automatic air conditioner drain system sanitizer 10, according to a method of use of the present invention, shown fitted to an component mounting panel 932 of a waterproof enclosure 930; power is provided utilizing a solar panel 936, a solar panel charge controller 938, and on-board rechargeable battery 934;

Figure 1:
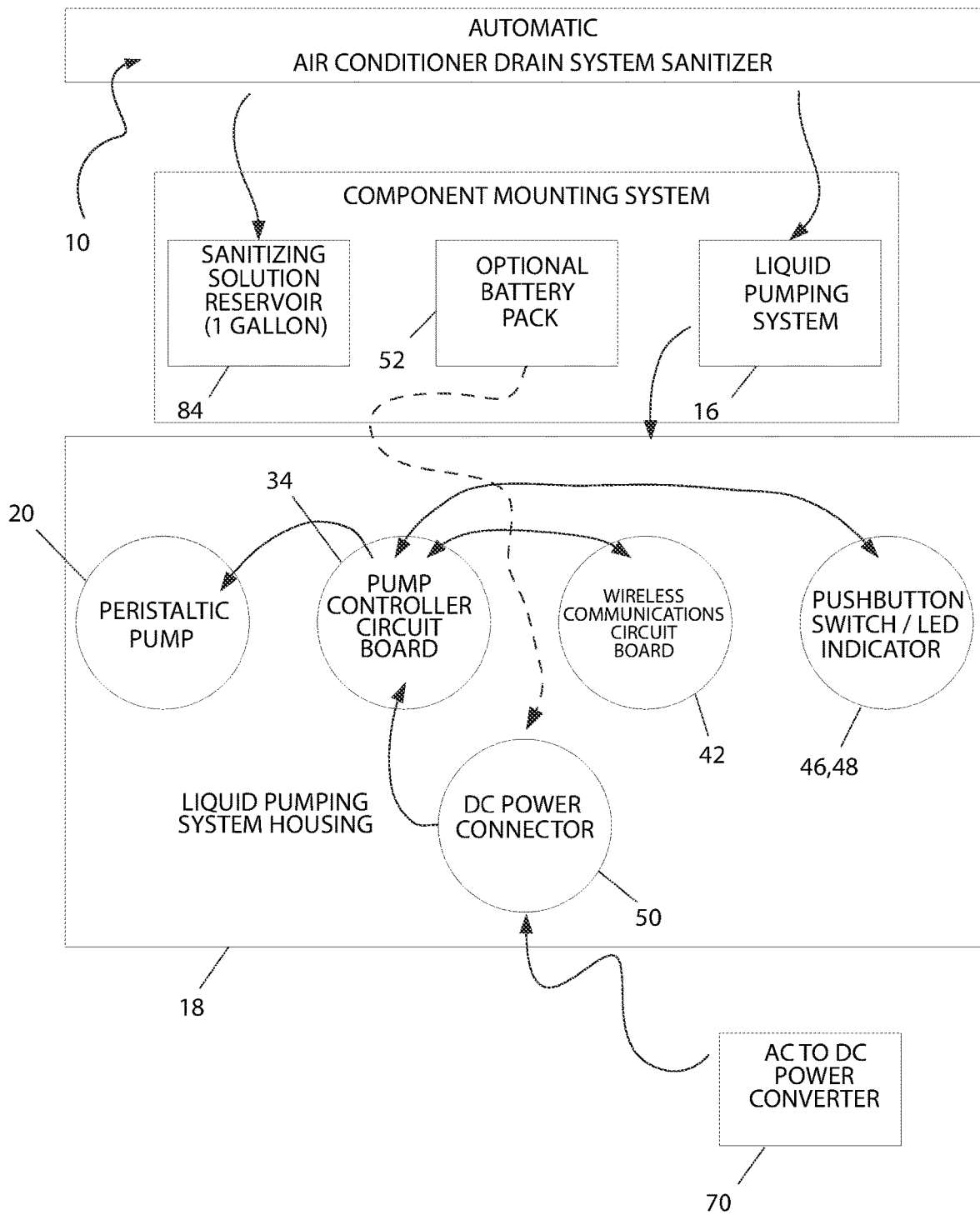
FIG. 1 is a pictorial view of an automatic air conditioner drain system sanitizer 10, showing the various system components.
Figure 2:
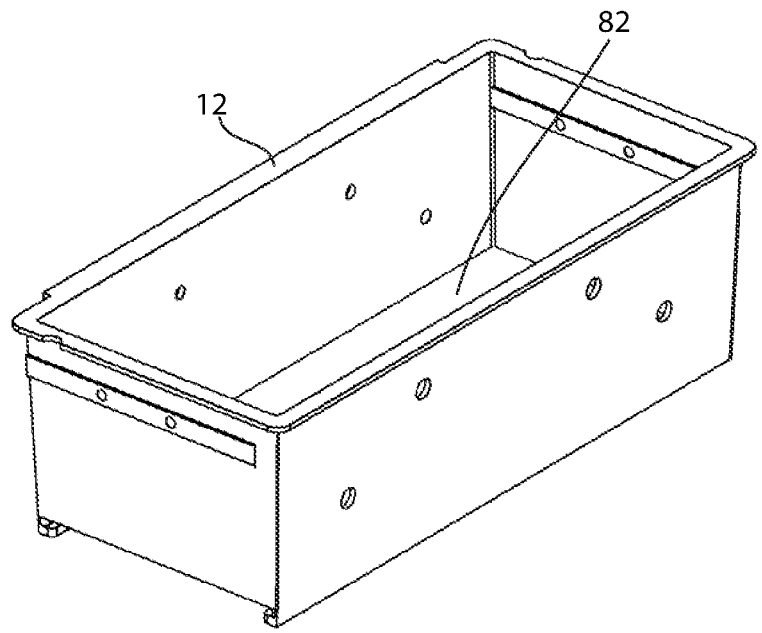
FIG. 2 is an isometric front view of an automatic air conditioner drain system sanitizer 10, according to an embodiment of the present invention, illustrating the component mounting fixture 12.
Figure 3:
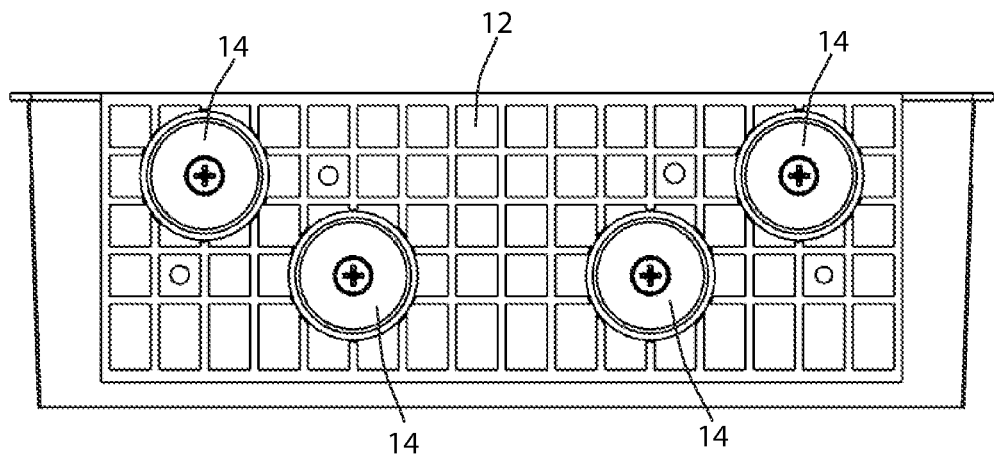
FIG. 3 is an orthogonal view of an automatic air conditioner drain system sanitizer 10, according to an embodiment of the present invention, illustrating the rear face of the component mounting fixture 12, and four (4) circular mounting magnets 14.
Figure 4:
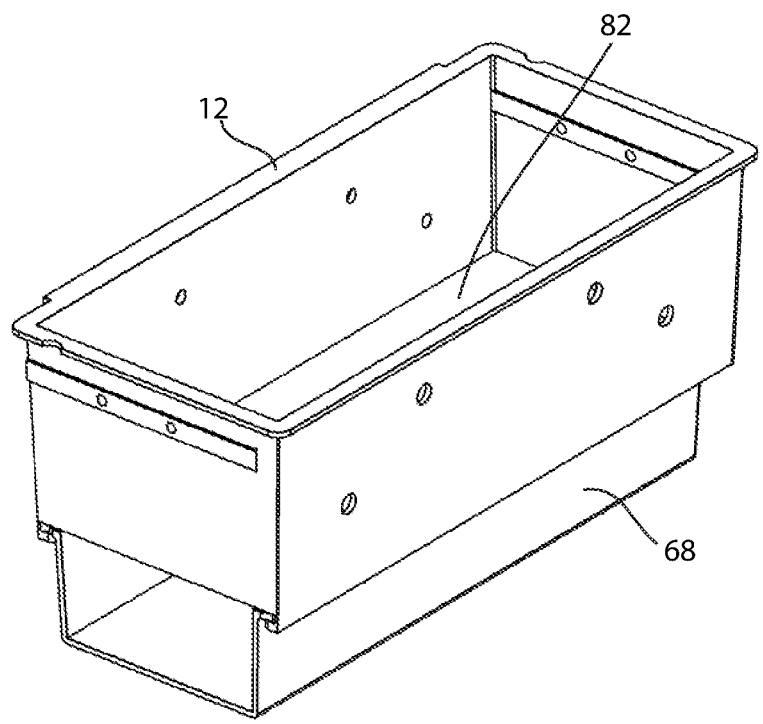
FIG. 4 is an isometric front view of an automatic air conditioner drain system sanitizer 10, according to an embodiment of the present invention, illustrating the component mounting fixture 12 with the optional battery pack holding tray 68 attached.
Figure 5:
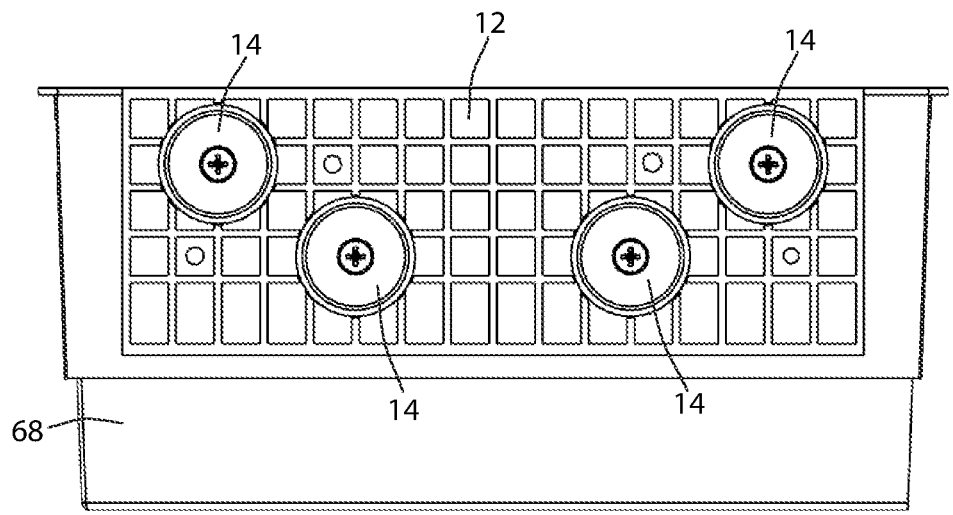
FIG. 5 is an orthogonal rear view of an automatic air conditioner drain system sanitizer 10, according to an embodiment of the present invention, illustrating the rear face of the component mounting fixture 12, four (4) circular mounting magnets 14, and with the optional battery pack holding tray 68 attached.
Figure 6:
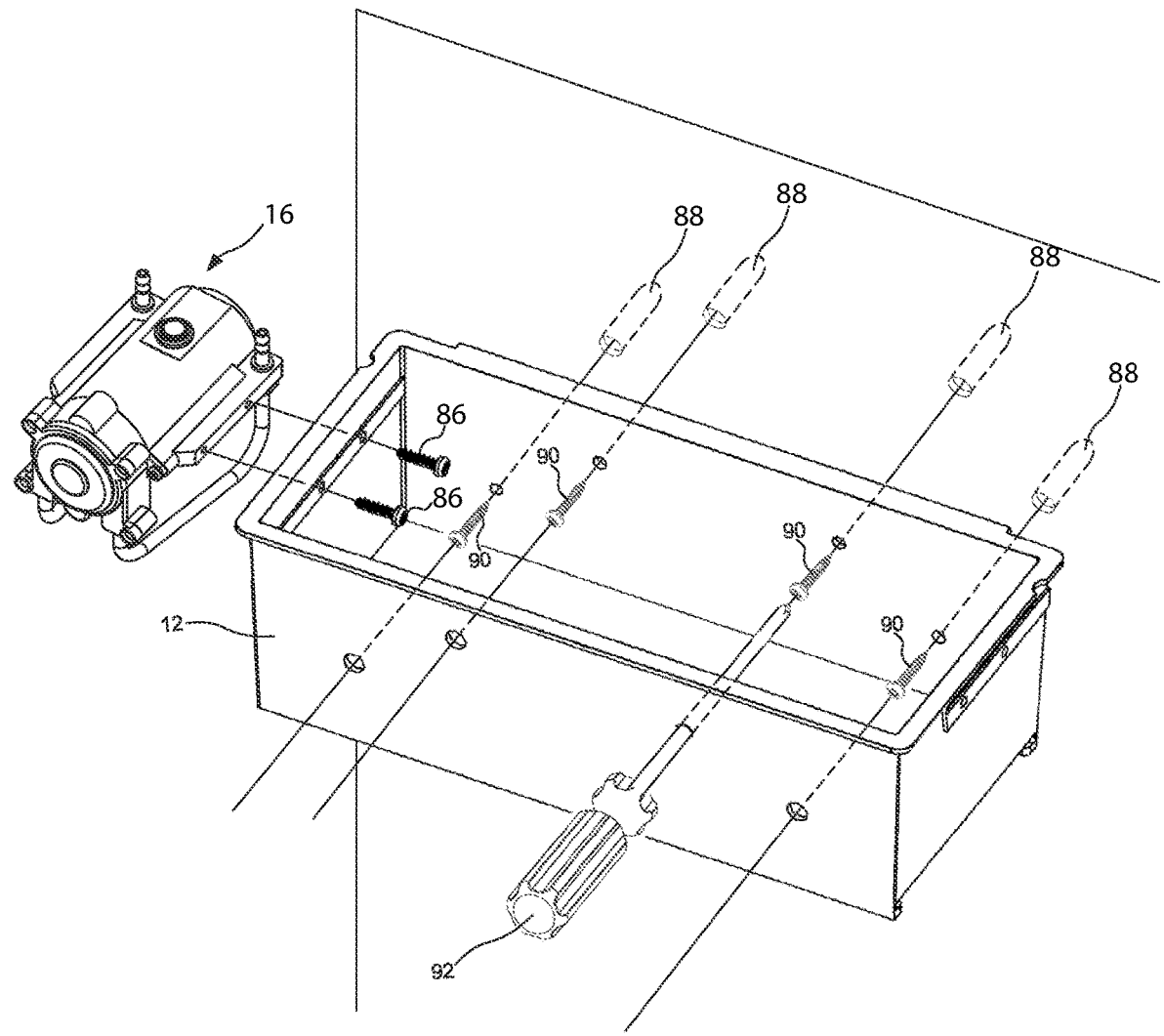
FIG. 6 is an isometric front view of an automatic air conditioner drain system sanitizer 10, according to an embodiment of the present invention, illustrating the component mounting fixture 12 being mechanically fastened to a non-steel surface utilizing wall anchors 88 and machine screws 90, and showing the attachment of the liquid pumping system 16 with a mechanical fastener.
Figure 7:
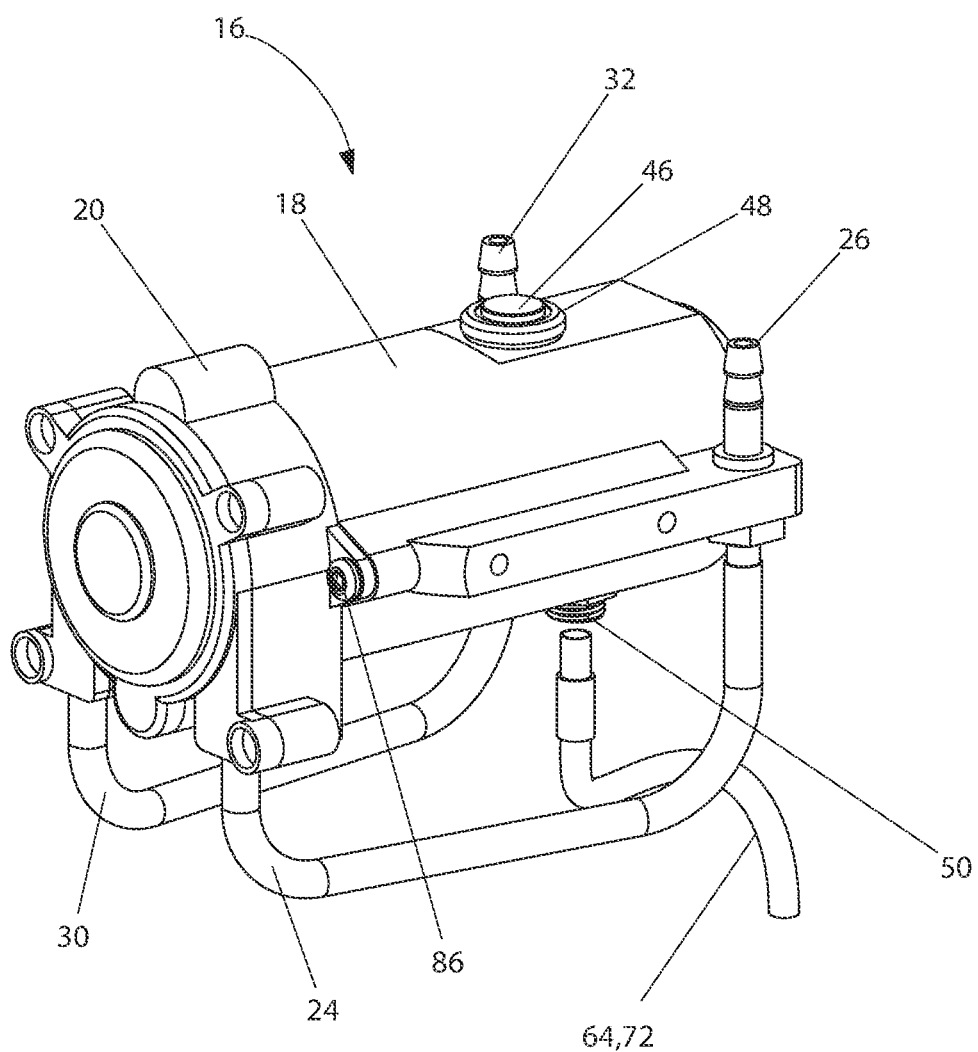
FIG. 7 is an isometric front view of an automatic air conditioner drain system sanitizer 10, according to an embodiment of the present invention, illustrating the liquid pumping system 16.
Figure 8:
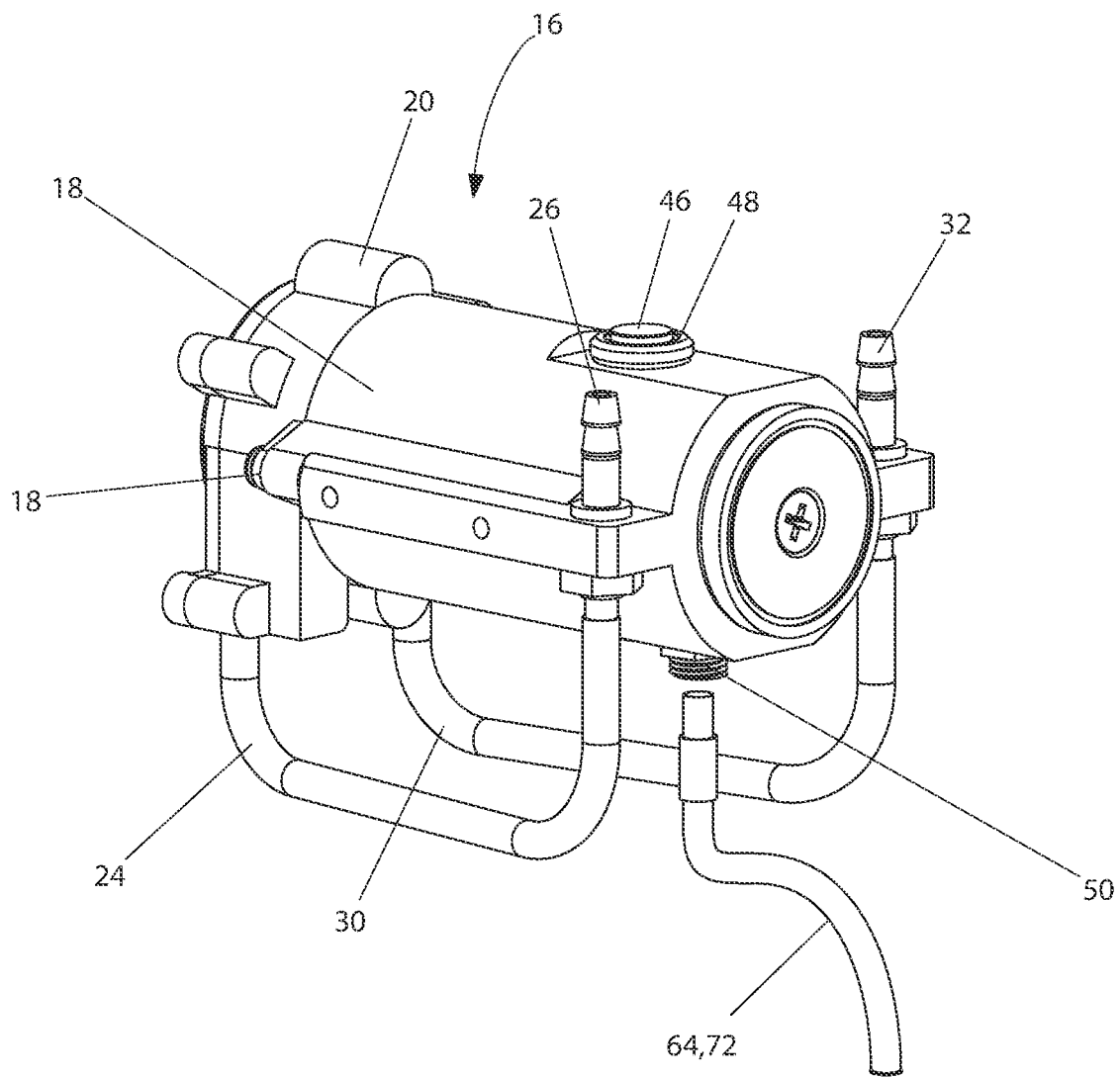
FIG. 8 is an isometric rear view of an automatic air conditioner drain system sanitizer 10, according to an embodiment of the present invention, illustrating the liquid pumping system 16.
Figure 9:
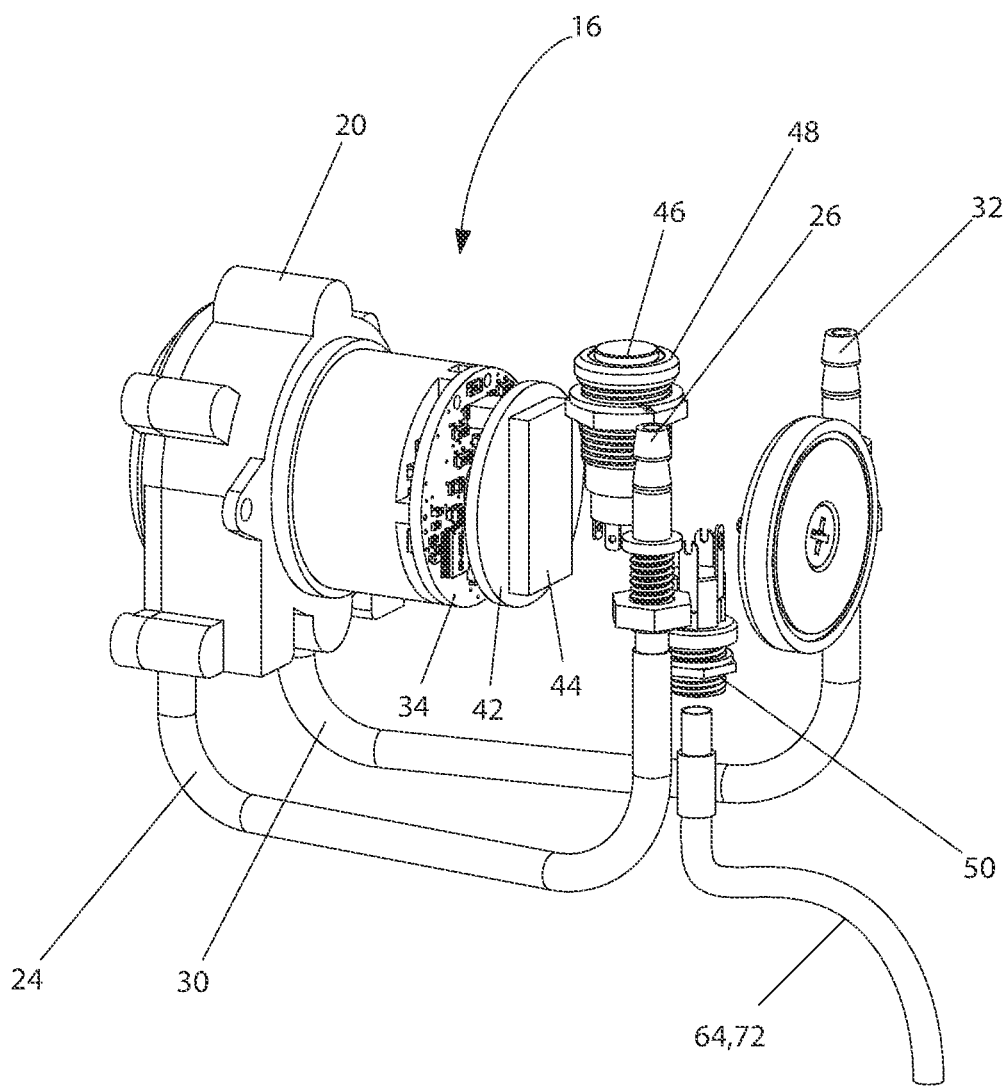
FIG. 9 is an isometric rear left side view of an automatic air conditioner drain system sanitizer 10, according to an embodiment of the present invention, illustrating the liquid pumping system 16.
Figure 10:
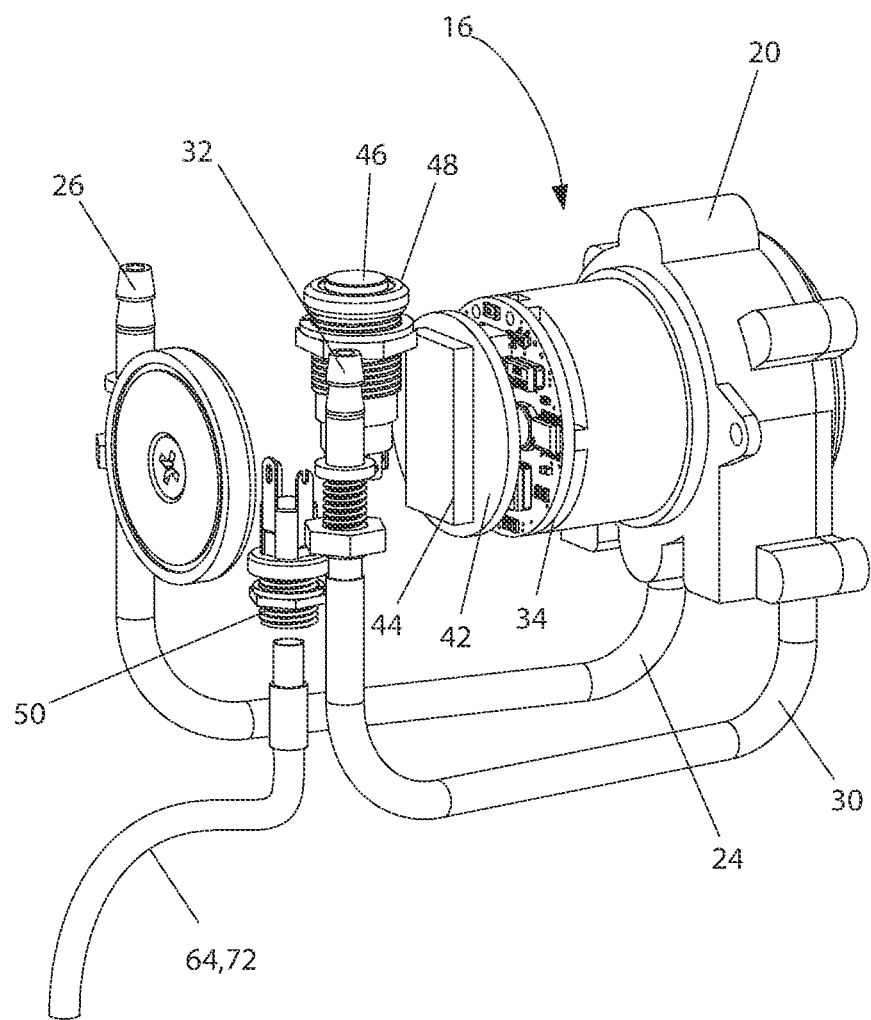
FIG. 10 is an isometric rear right side view of an automatic air conditioner drain system sanitizer 10, according to an embodiment of the present invention, illustrating the liquid pumping system 16.
Figure 11:
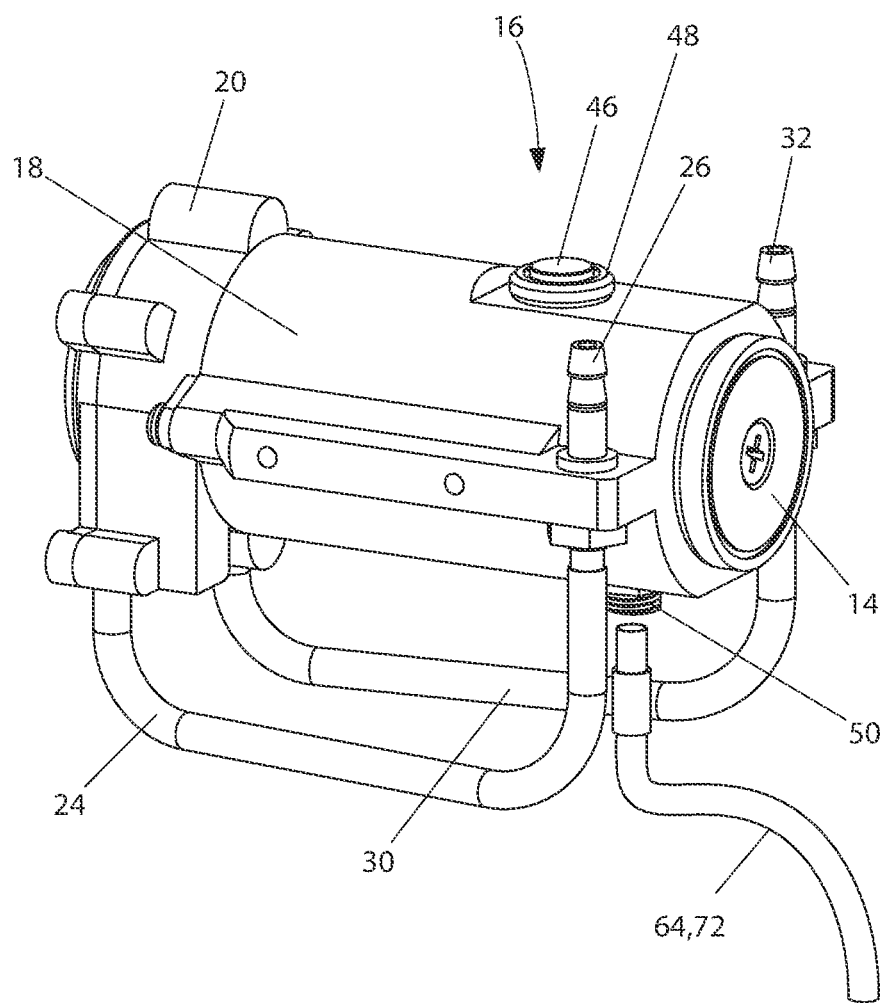
FIG. 11 is an isometric rear left side view of an automatic air conditioner drain system sanitizer 10, according to an embodiment of the present invention, illustrating the liquid pumping system 16 coupled with an optional circular mounting magnet 14.
Figure 12A:
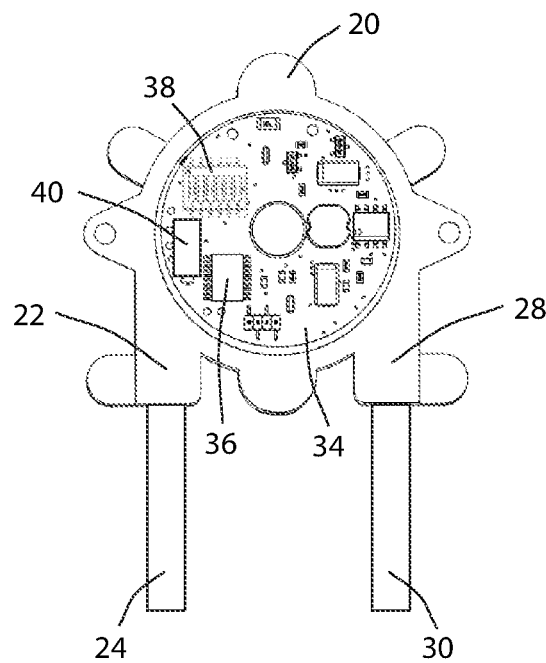
FIG. 12a is an orthogonal front view of an automatic air conditioner drain system sanitizer 10, according to an embodiment of the present invention, illustrating the pump controller circuit board 34.
Figure 12B:
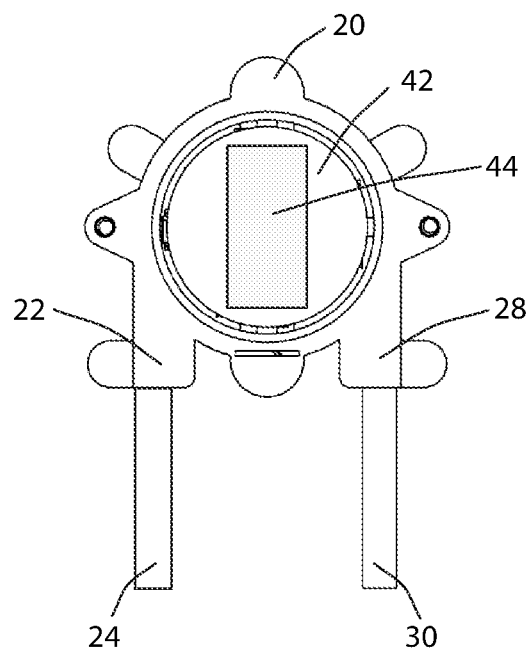
FIG. 12b is an orthogonal front view of an automatic air conditioner drain system sanitizer 10, according to an embodiment of the present invention, illustrating the wireless communication circuit board 42.
Figure 13A:
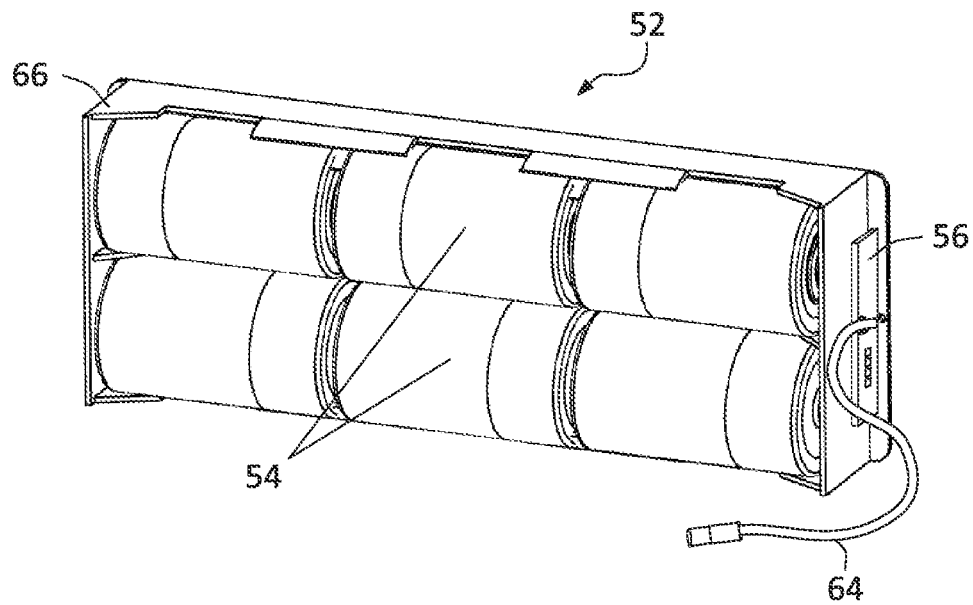
FIG. 13a is an isometric top view of an automatic air conditioner drain system sanitizer 10, according to an embodiment of the present invention, illustrating the optional battery pack 52.
Figure 13B:
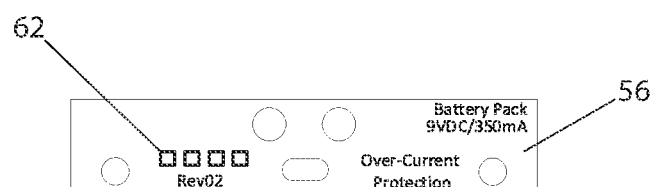
FIG. 13b is an orthogonal front view of an automatic air conditioner drain system sanitizer 10, according to an embodiment of the present invention, illustrating the optional battery pack circuit board 56.
Figure 13C:
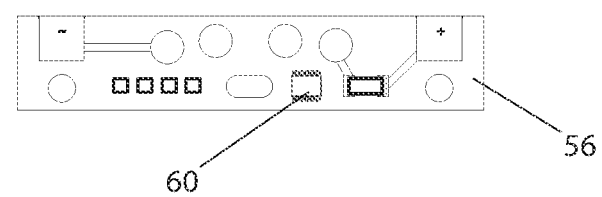
FIG. 13c is an orthogonal rear view of an automatic air conditioner drain system sanitizer 10, according to an embodiment of the present invention, illustrating the optional battery pack circuit board 56.
Figure 14:
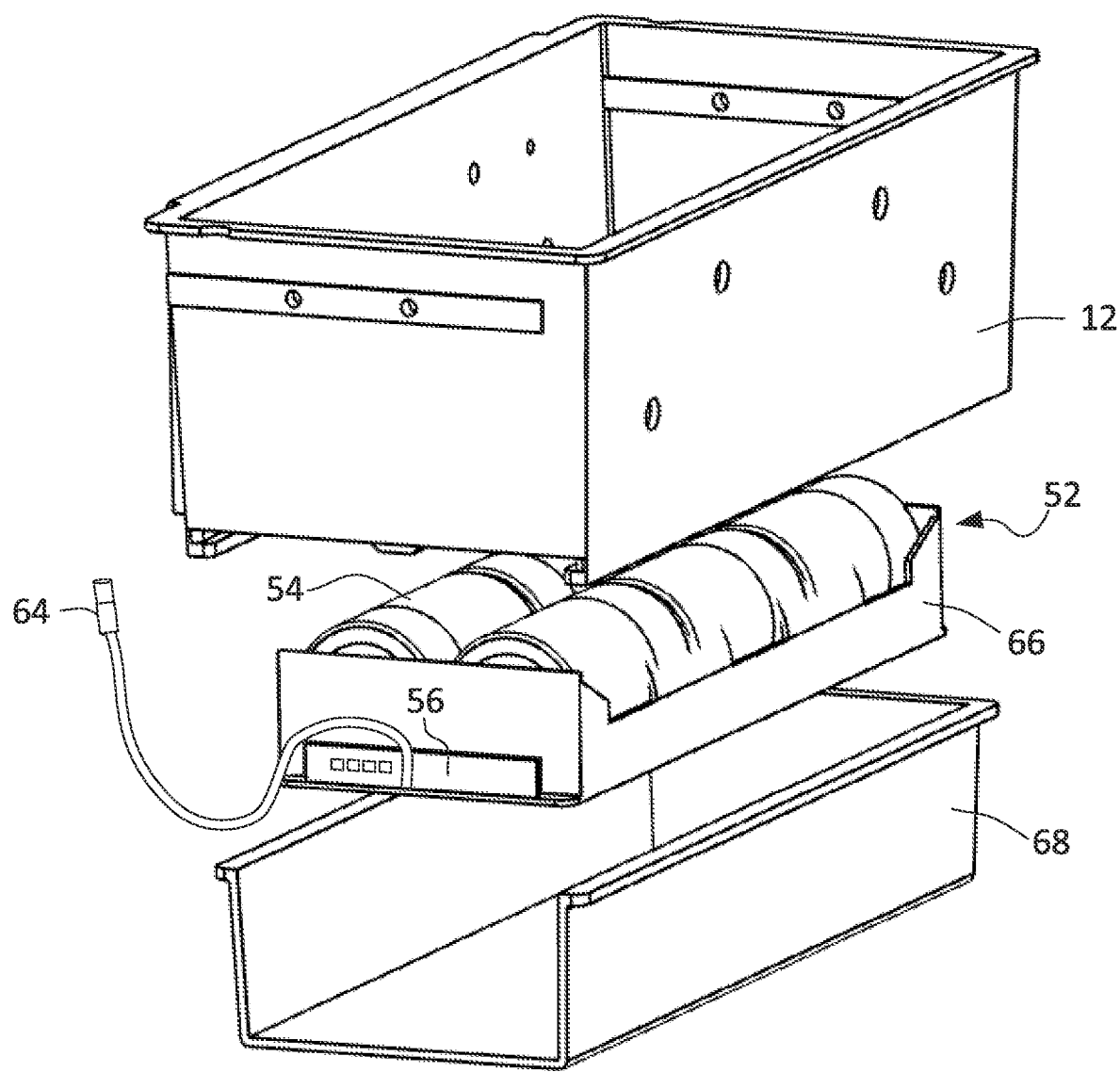
FIG. 14 is an isometric front view of an automatic air conditioner drain system sanitizer 10, according to an embodiment of the present invention, illustrating the component mounting fixture 12, optional battery pack 52, and optional battery pack holding tray 68.
Figure 15:
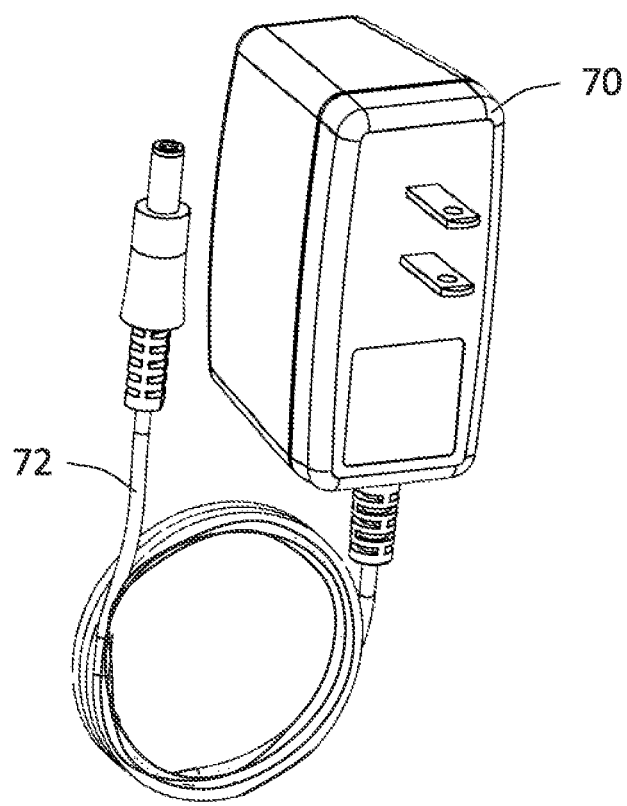
FIG. 15 is an isometric view of an automatic air conditioner drain system sanitizer 10, according to an embodiment of the present invention, illustrating the AC to DC power converter 70.
Figure 16:
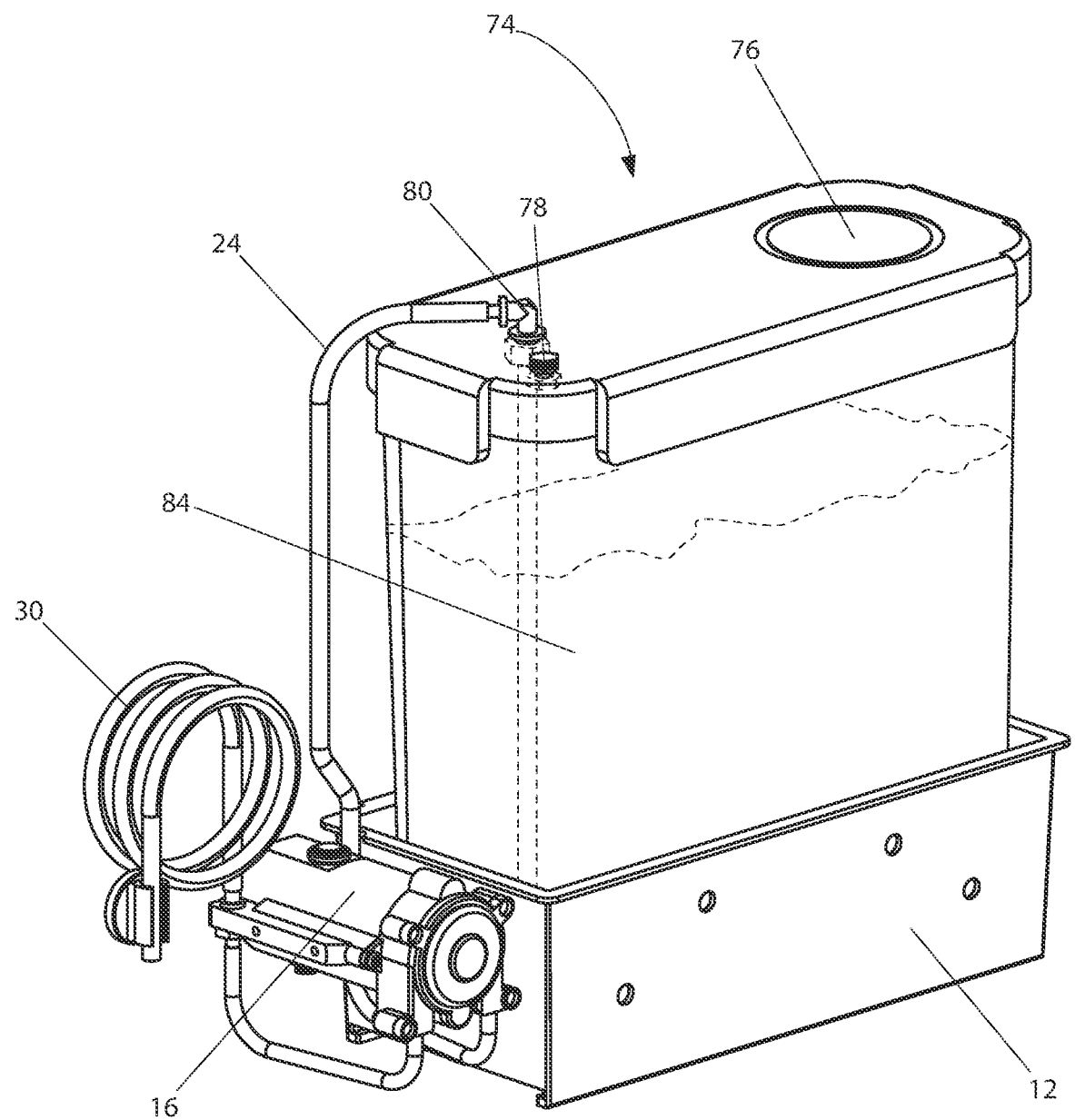
FIG. 16 is an isometric front view of an automatic air conditioner drain system sanitizer 10, according to an embodiment of the present invention, illustrating the fitting of various system components.
Figure 17:
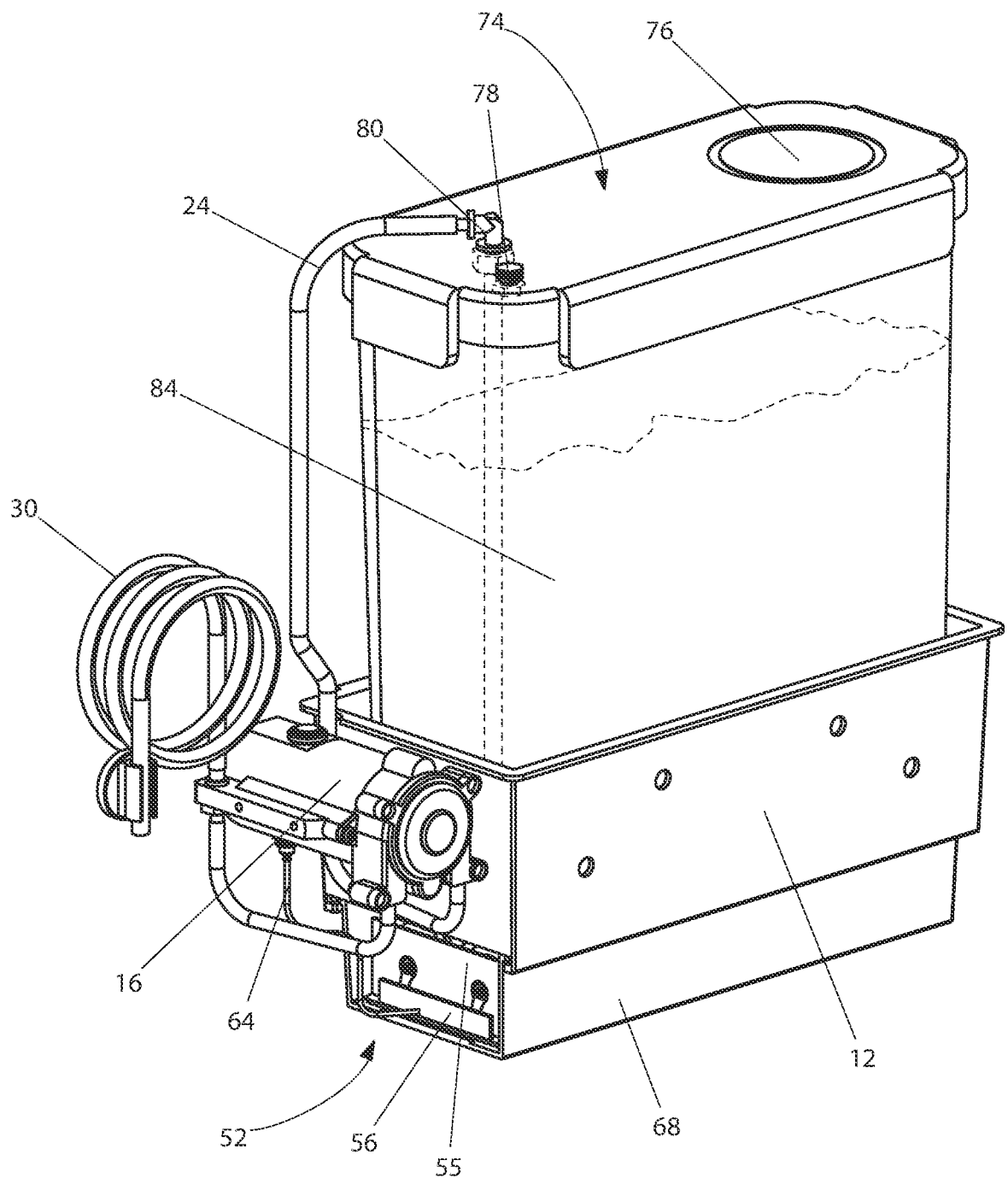
FIG. 17 is an isometric front view of an automatic air conditioner drain system sanitizer 10, according to an embodiment of the present invention, illustrating the fitting of various system components including the optional battery pack holding tray 68 and battery pack 52.
Figure 18:
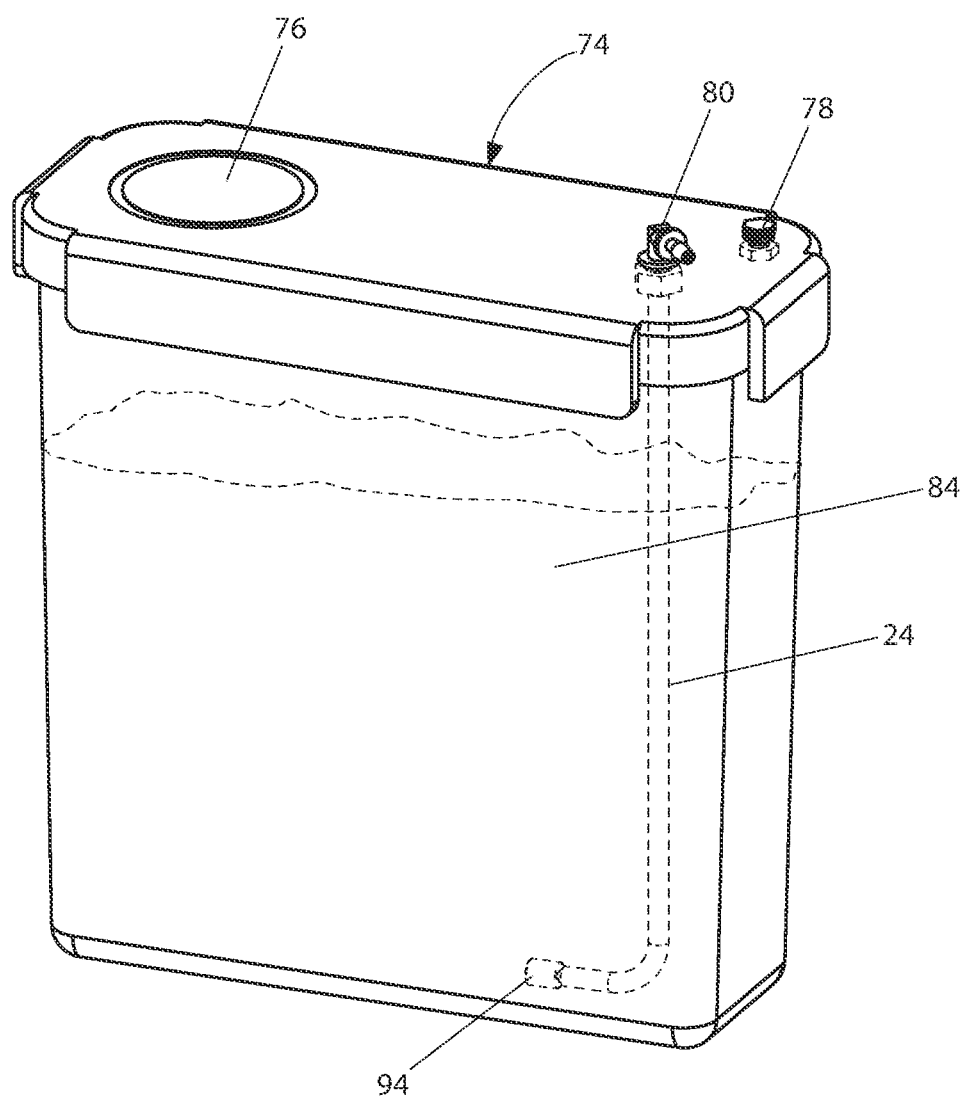
FIG. 18 is an isometric front view of an automatic air conditioner drain system sanitizer 10, according to an embodiment of the present invention, illustrating the drain sanitizer solution reservoir 74.
Figure 19A:
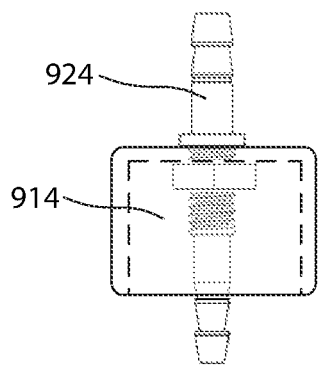
FIG. 19*a* is an cut-away side view of an automatic air conditioner drain system sanitizer 10, according to an embodiment of the present invention, illustrating a modified three-quarter inch (¾ in.) slip-on condensate drain line access port cap 914 fitted with a pass-through bulkhead tubing coupler 924.
Figure 19B:
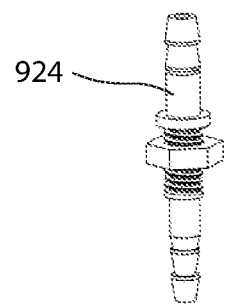
FIG. 19*b* is an orthogonal side view of an automatic air conditioner drain system sanitizer 10, according to an embodiment of the present invention, illustrating a pass-through bulkhead tubing coupler 924.
Figure 19C:
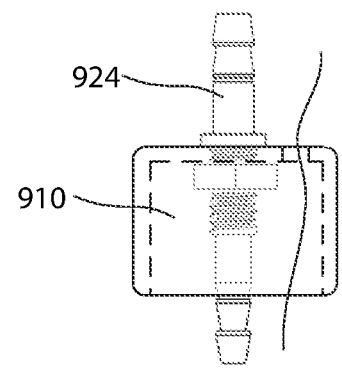
FIG. 19*c* is an cut-away side view of an automatic air conditioner drain system sanitizer 10, according to an embodiment of the present invention, illustrating a modified three-quarter inch (¾ in.) slip-on condensate drain line vent tube cap 910 with an aperture and fitted with a pass-through bulkhead tubing coupler 924.
Figure 20A:
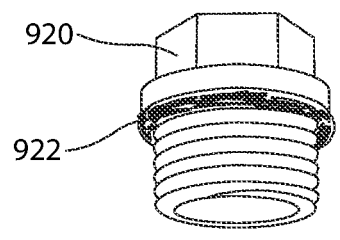
FIG. 20*a* is an orthogonal side view of an automatic air conditioner drain system sanitizer 10, according to an embodiment of the present invention, illustrating a modified condensate drain pan outlet port plug 920 fitted with a condensate drain pan outlet port plug 920.
Figure 20B:
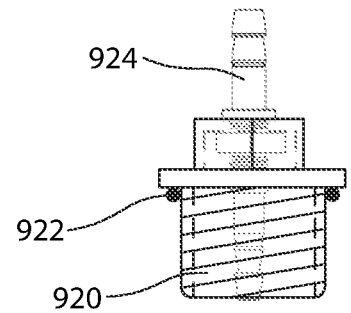
FIG. 20*b* is a cut-away side view of an automatic air conditioner drain system sanitizer 10, according to an embodiment of the present invention, illustrating a modified condensate drain pan outlet port plug 920 fitted with a pass-through bulkhead tubing coupler 924 and a condensate drain pan outlet port plug 920.
Figure 21A:
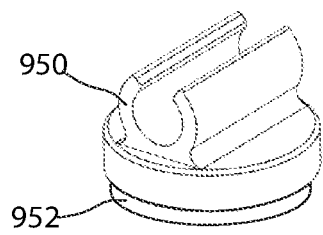
FIG. 21*a* is an orthogonal side view of an automatic air conditioner drain system sanitizer 10, according to an embodiment of the present invention, illustrating a discharge tube holder 950.
Figure 21B:
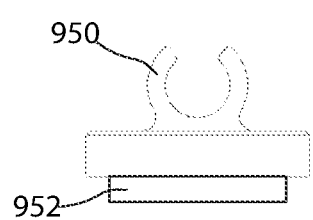
FIG. 21*b* is a side elevation view of an automatic air conditioner drain system sanitizer 10, according to an embodiment of the present invention, illustrating a discharge tube holder 950.
Figure 21C:
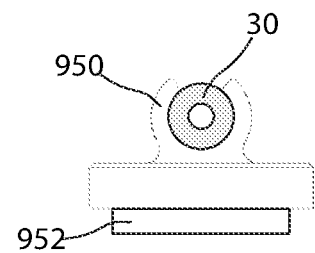
FIG. 21*c* is a side elevation view of an automatic air conditioner drain system sanitizer 10, according to an embodiment of the present invention, illustrating a discharge tube holder 950 holding a portion of a discharge tube 30.

DESCRIPTIVE KEY 10 automatic air conditioner drain system sanitizer
12 component mounting fixture
14 circular mounting magnet
16 liquid pumping system
18 liquid pumping system housing
20 peristaltic pump
22 pump inlet
24 intake tubing
26 intake tubing coupler
28 pump outlet
30 discharge tubing
32 discharge tubing coupler
34 pump controller circuit board
36 microcontroller
38 multi-position switch array
40 supercapacitor
42 wireless communications circuit board
44 wireless communications module 46 pushbutton switch
48 pushbutton switch LED indicator light
50 DC power connector
52 battery pack
54 battery
56 battery pack circuit board
58 battery pack circuit board electronic current-limiter
60 battery pack circuit board microcontroller
62 battery pack power level LED indicator
64 battery pack DC power cable
66 battery holder
68 battery pack holding tray
70 AC to DC power converter
72 AC to DC power converter power cable
74 drain sanitizer solution reservoir
76 drain sanitizer solution reservoir lid
78 drain sanitizer solution reservoir atmospheric equalizing vent
80 drain sanitizer solution reservoir tubing coupler
82 drain sanitizer solution reservoir holding section
84 drain sanitizer solution
86 thread-forming screw
88 wall anchor
90 machine screw
92 Phillips-type screwdriver
94 aerator
900 evaporator
902 evaporator condensate collection drain pan
904 condensate collection and removal drain system
906 condensate drain line
908 condensate drain line vent tube
910 condensate drain line vent tube cap
912 condensate drain line access port
914 condensate drain line access port cap
916 condensate drain line "P" trap
918 condensate drain pan outlet port
920 condensate drain pan outlet port plug
922 condensate drain pan outlet port plug sealing O-ring
924 pass-through bulkhead tubing coupler
926 backup detection switch
928 overflow drain pan
930 outdoor-rated waterproof enclosure
932 component mounting panel
934 rechargeable battery
936 solar panel
938 solar panel charge controller
940 commercial roof-mounted air conditioning system
942 solar-powered outdoor-rated automatic AC drain line sanitizer
944 main electrical cable
946 see-through window
948 health status indicator LED
950 discharge tube holder
952 discharge tube holder magnet

DETAILED DESCRIPTION

The present invention is directed to an automatic air conditioner drain system sanitizer (herein described as the "invention") 10. The automatic air conditioner drain system sanitizer 10 may comprise a component mounting fixture 12, a liquid pumping system 16, a drain sanitizer solution reservoir 74, and a power source. The automatic air conditioner drain system sanitizer 10 may be configured to dispense a drain sanitizer solution 84 from the drain sanitizer solution reservoir 74 directly into an air conditioner evaporator condensate collection drain pan 902 or condensate drain line 906 periodically in order to prevent growth of microorganisms within the condensate collection and removal drain system 904. The microorganisms may be referred to as white slime and may comprise bacteria, algae, mold, mildew, fungus, or any combination thereof. As non-limiting examples, the drain sanitizer solution 84 may be distilled white vinegar, bleach, chlorine, drain sanitizing tablets dissolved in water, or a liquid drain line clearing product. The settings for the quantity of drain sanitizer solution 84 dispensed and the dispensing interval frequency will be factory set to default parameters and may be modified if desired. Dispensing one-half to one cup (½-1 c) of the drain sanitizer solution 84 once or twice a month may be typical. Based upon system variations, including, but not limited to: the type of drain sanitizer solution 84 used, or different pumping applications, the default parameters may be modified by the user.

The liquid pumping system 16 may move the drain sanitizer solution 84 from a pump inlet 22 to a pump outlet 28. The peristaltic pump 20 may be electromechanical and may comprise an internal motor that may be energized by the application of a pump activation signal to the peristaltic pump 20. As non-limiting examples, the peristaltic pump 20 may move the drain sanitizer solution 84 by applying rotary motion, reciprocating motion, linear motion, or a combination thereof to one (1) or more gears, screws, pistons, rollers, shuttle blocks, vanes, diaphragms, plungers, impellers, or combinations thereof. The peristaltic pump 20 may draw the drain sanitizer solution 84 into the peristaltic pump 20 from the drain sanitizer solution reservoir 74 through intake tubing 24 that is coupled via fluid communication to the pump inlet 22 via an intake tubing coupler 26. The peristaltic pump 20 may discharge the drain sanitizer solution 84 through discharge tubing 30 that is coupled via fluid communication to the pump outlet 28 via a discharge tubing coupler 32.

In a preferred embodiment, the liquid pumping system 16 may comprise a peristaltic pump 20. A peristaltic pump 20 may be a type of positive displacement fluid transfer device for pumping a fluid using the rotary motion of a number of rollers within the peristaltic pump 20 to force the fluid through an internal flexible tube. Pump rotation direction is selectable by the microcontroller 36. Operating the pump in a counterclockwise direction will force air into the drain sanitizer solution reservoir 74 through an aerator 94 with the resulting bubbles created by the air inflow enabling the drain sanitizer solution 84 to mix homogeneously, thereby preventing any material settling of the drain sanitizer solution 84. A peristaltic pump 20 was selected for this application due to many inherent benefits of a peristaltic pump 20 head design. As examples and not limited to: the drain sanitizer solution 84 does not contact the pump mechanism as the fluid is contained inside the tubing, allowing harsh chemicals to be dispensed if required by the application; the 15 pump mechanism requires no cleaning of valves, seals, or diaphragms; a peristaltic pump 20 is highly accurate and repeatable in quantity of liquid dispensed; a peristaltic pump 20 is classified as self-priming, which means the peristaltic pump 20 can draw fluids into the pump from a dry start requiring no operator intervention to initiate the liquid transfer; a peristaltic pump 20 is non-siphoning, meaning no liquid is transferred back into the drain sanitizer solution reservoir 74 when the peristaltic pump 20 is deenergized, regardless of whether the peristaltic pump 20 is mounted above, or below, the dispensing location. A practical in-use example of this non-siphoning feature is the liquid pumping system 16 may be elevated multiple meters above the drain sanitizer solution reservoir 74 and the liquid pumping system 16 may draw the liquid up into and the pump mechanism. When the peristaltic pump 20 is deenergized, liquid will not flow backwards to the drain sanitizer solution reservoir 74, the liquid will remain stationary within the discharge tubing 30 ready for the next pumping cycle. For a typical air conditioner attic installation, (see FIG. 22*e*) if attic access is unrestricted, the liquid pumping system 16 may be mounted adjacent to the evaporator 900, or if attic access is difficult, due to the positive displacement and anti-siphoning functions of the peristaltic pump 20, the automatic air conditioner drain system sanitizer 10 may be located on a lower floor with the drain sanitizer solution 84 pumped up into the attic. This installation example allows unfettered access to the liquid pumping system 16 for re-filling of the drain sanitizer solution reservoir 74 and, if needed, batteries 54 replacement. The self-priming and anti-siphoning functions of the peristaltic pump 20 eliminates the needs for anti-reverse flow check-valves and complicated plumbing arrangements with multiple tubing connections which are prone to potential leaks. Only a single pump is required for the application. For all of the above benefits mentioned, a peristaltic pump 20 was selected.

The pump controller circuit board 34 may control the operation of the automatic air conditioner drain system sanitizer 10. The pump controller circuit board 34 may track time, may determine when to dispense the drain sanitizer solution 84, may energize the peristaltic pump 20 by applying the pump activation signal to the motor drive circuit, may control pump rotation direction, may control the quantity of the drain sanitizer solution 84 dispensed via the duration of the pump activation signal, and may deenergize the peristaltic pump 20. It is envisioned that the pump controller circuit board 34 may be capable of wireless communication with a dedicated application for wireless control thereof.

The pump controller circuit board 34 may comprise a microcontroller 36. The microcontroller 36 may be a computer processor that incorporates the functions of a central processing unit in the form of one (1) or more integrated circuits. The microcontroller 36 may be a multipurpose, clock driven, register based, digital-integrated circuit. The microcontroller 36 may accept binary data as input, may process the binary data according to instructions stored in memory contained within the microcontroller 36, and may provide results as output. The microcontroller 36 may contain both combinational logic and sequential digital logic. The microcontroller 36 may operate on numbers and symbols represented in the binary number system.

The binary data comprising inputs and the results comprising outputs may relate to control signals received from and provided to other circuitry. As non-limiting examples, the microcontroller 36 may receive inputs from internal high-accuracy crystal-controlled timers and may control outputs coupled to an on-board motor drive circuit. The microcontroller 36 may count clock ticks in order to track elapsed time. As a non-limiting example, the microcontroller 36 may track the passage of milliseconds and, by counting milliseconds, may be further operable to track the passage of seconds, minutes, hours, days, weeks, months, years, or any combination thereof. In some embodiments, the microcontroller 36 may be operable with various internal high-accuracy crystal-controlled timers to precisely wakeup the microcontroller 36 from a sleep state on a periodic basis and/or after an elapsed time interval.

The pump controller circuit board 34 may comprise various circuit components to facilitate ultra-low power consumption operation, circuit signal integrity and reliable operating stability. As non-limiting examples, the pump controller circuit board 34 may rectify the input power to prevent damage from reversed polarity, may filter the input power to prevent operational issues due to noisy power supplies, may limit the current draw from the incoming power source, may measure the voltage level of the input power, may measure motor current to verify proper pump motor operation, or any combination thereof.

In some embodiments, the pump controller circuit board 34 may comprise a supercapacitor 40 to power the microcontroller 36 during power interruptions. A microcontroller 36 internal real-time clock (RTC) may provide operation input based upon set seconds/days/months/years or any combination thereof. Microcontroller 36 internal electrically erasable programmable read-only memory (EEPROM) may be utilized to store critical operating parameters and settings. The operational parameters may be set to factory default settings, which under normal air conditioner sanitizing applications, would not need to be modified yet are available to be operator-modified for potential diverse pumping applications.

The pump controller circuit board 34 may convert one (1) or more digital outputs from the microcontroller 36 into the pump activation signal that may energize the peristaltic pump 20 through bi-directional motor drive circuitry. During operation, the microcontroller 36 enters a low power sleep state for approximately thirty seconds (30 s), then wakes up and illuminates a green pushbutton switch LED indicator 48 for one second (1 s) to signify that the system operational status is nominal. If the voltage level of the optional battery pack 52 reaches a minimum value that the liquid pumping system 16 can't reliably pump any longer, the pushbutton switch LED indicator 48 will flash every two seconds (2 s) signaling the batteries 54 must be changed. If the system is running on AC power via the AC to DC power converter 70, the sleep/wakeup operating process is identical and the pushbutton switch LED indicator 48 will illuminate every thirty seconds (30 s), as the incoming DC power level will always be at maximum. In the event the microcontroller 36 senses a system fault, the pushbutton switch LED indicator 48 will illuminate at a frequency which corresponds to the fault, and the fault frequency can readily be looked up in the operations manual.

The liquid pumping system 16 may further comprise a liquid pumping system housing 18 which incorporates the pump controller circuit board 34, a wireless communication circuit board 42 with an onboard wireless communications module 44, the peristaltic pump 20, DC power connector 50 and a momentary pushbutton switch 46. The liquid pumping system housing 18 is coupled to the component mounting fixture 12 with a single stainless-steel thread forming screw 86. A DC power connector 50 may be accessible outside of the liquid pumping system housing 18.

The liquid pumping system housing 18 may be opened to access a multi-position switch array 38 located on the pump controller circuit board 34. The multi-position switch array 38 may be used for setting additional operational parameters and allow for future system customization and/or upgrades.

The operator interface may be comprised of a momentary pushbutton switch 46 with a pushbutton switch LED indicator 48. The pushbutton switch LED indicator 48 will flash periodically providing the pump controller circuit board 34 and wireless communications circuit board 42 health status. The momentary pushbutton switch 46 provides for various functions, which may include but are not limited to: direct manual pump activation, incoming DC power level indication and modification of the dispense quantity timing and dispense interval frequency. Various functions of the user interface may be accessed by pressing the momentary pushbutton switch 46 one (1) or more times to activate a response from the microcontroller 36, thereby initiating one (1) of several pre-programmed system utilities. As examples, but not limited to: pressing and continuously holding the momentary pushbutton switch 46 will activate the peristaltic pump 20 in the clockwise direction which will dispense a drain sanitizer solution 84 into the condensate collection and removal drain system 904; an additional function may be two pressings of the momentary pushbutton switch 46 which will initiate a manual mixing/oxygenation cycle; an additional function may be three pressings of the momentary pushbutton switch 46 which will initiate pumping one-half cup (½ c) of the sanitizing solution 84; an additional function may be five (5) pressings of the momentary pushbutton switch 46 which will initiate a program modification mode where further pressing of the momentary pushbutton switch 46 selects a different pre-programmed combination of dispense quantity timing and dispense interval frequency. If a different combination of dispense quantity timing and dispense interval frequency is selected, the new settings will be saved in the microcontroller 36 EEPROM permanently. Utilizing a momentary pushbutton switch 46 based method for selecting multiple system functions and allowing modifications to the dispensing parameters, combined with a six-position on-board switch array, allows for flexible operation options of the automatic air conditioner drain system sanitizer 10, and for customization of additional applications with no hardware changes.

The drain sanitizer solution reservoir 74 may store the drain sanitizer solution 84 prior to dispensing. The drain sanitizer solution reservoir 74 resides in a drain sanitizer solution reservoir holding section 82 of the component mounting fixture 12. As non-limiting examples, the drain sanitizer solution reservoir 74 may be a container with a drain sanitizer solution reservoir lid 76 enabling convenient filling/re-filling, may include an atmospheric equalizing vent 78 and a drain sanitizer solution reservoir tubing coupler 80. The intake tubing 24 may fluidically pass through the drain sanitizer solution reservoir tubing coupler 80 on the drain sanitizer solution reservoir 74 in order to reach the drain sanitizer solution 84.

The liquid pumping system 16 requires a nominal nine (9) volt DC voltage power source. If an AC electrical outlet is available in the vicinity of the air conditioning system, the power source may be an AC to DC power converter 70 (supplied) that may plug into the DC power connector 50 located on the underside of the liquid pumping system housing 18. A generous ten-foot (10 ft.) length of DC power converter power cable 72 is provided. If an AC outlet is not available, the pump controller circuit board 34 may be powered from a battery pack 52. The battery pack 52 may comprise a plurality of batteries 54 inserted into a battery holder 66 that may be mounted in close proximity to the liquid pumping system housing 18. The battery pack 52 may be inserted horizontally into a optional battery pack holding tray 68. The optional battery pack holding tray 68 is physically coupled to the component mounting fixture 12 by sliding the optional battery pack holding tray 68 into mating molded tracks on the component mounting fixture 12. A optional battery pack circuit board 56 is coupled to the battery holder 66, and may comprise an electronic current-limiter 58, a microcontroller 60, connection of a battery pack DC power cable 64 with a male five-point-five by two-point-one millimeter (5.5 mm×2.1 mm) barrel-type connector, and a multi-color array of four (4) battery power level LED indicators 62. The microcontroller 60 will illuminate, at thirty second (30 s) intervals, one (1) of the battery power level LED indicators 62 corresponding to the battery pack 52 state-of-charge remaining. When one (1) of the battery power level LED indicators 62 is illuminated, the color illuminated corresponds directly to a percentage of the current state-of-charge of the battery pack 52. The battery power level LED indicators 62 colors may be green, orange, yellow and red. Green corresponds to a state-of-charge of one hundred to eighty percent (100 to 80%), orange corresponds to a state-of-charge of seventy-nine to forty percent (79 to 40%), yellow corresponds to a state-of-charge of thirty-nine to ten percent (39 to 10%) and red corresponds to a state-of-charge of nine to zero percent (9 to 0%). If a red battery power level LED indicators 62 illuminates, the batteries 54 are at a minimum state-of-charge and should be changed soon. Depending on the color of the LED indicator 62 which is illuminated, an approximate conversion of the state-of-charge of the batteries 54 to months remaining before the batteries 54 are required to be changed would be: green=twelve to ten months (12 to 10 mo.); yellow=ten to six months (10 to 6 mo.); orange=six to three months (6 to 3 mo.); a different yellow=three to one months (3 to 1 mo.); and red, less than one month (1 mo.) remaining. If the voltage level of the battery pack 52 reaches a minimum value that the liquid pumping system 16 can't reliably pump any longer, the red battery power level LED indicators 62 will flash every two seconds (2 s) signaling the batteries 54 must be changed immediately. The battery holder 66 is open to facilitate replacing the plurality of batteries 54. In a preferred embodiment, the battery pack 52 may contain six (6) D cell batteries 54 at a nine (9) volt full state-of-charge. The battery pack DC power cable 64 may be coupled to the DC power connector 50 of the liquid pumping system housing 18 to power the pump controller circuit board 34 from the battery pack 52. For additional unique pumping applications, any type of battery chemistry or combination of multiple batteries, including, but not limited to: on-board rechargeable battery 934, may be connected to the pump controller circuit board 34 with a maximum voltage level of 14 volts and must supply a minimum current level of three hundred fifty milliamps (350 mA). Multiple battery power solution options may provide for a much lengthier, if not unlimited, operational duration. For example, but not limited to: sanitizing the condensate collection and removal drain system 904 of a commercial roof-mounted air conditioning system 940 utilizing a solar power system 942. A solar panel 936 powered on-board rechargeable battery 934, whose state-of-charge level is electrically regulated by a solar panel charge controller 938, may be used to power the automatic air conditioner drain system sanitizer 10 which is fitted onto a component mounting panel 932 located inside of an waterproof enclosure 930. The unique design of the automatic air conditioner drain system sanitizer 10 provides a high degree of utilization flexibility for both indoor and outdoor applications.

In some embodiments, a plurality of circular mounting magnets 14 may be coupled to the rear face of the component mounting fixture 12 and may be operable to magnetically adhere the component mounting fixture 12 on metal surfaces such as the evaporator 900 housing. By utilizing four (4) circular mounting magnets 14, the installation of the automatic air conditioner drain system sanitizer 10 may not require any hand tools, which lends itself to a homeowner being able to install the system expeditiously and economically as no outside help is required. In some embodiments, there may be a single circular mounting magnet 14 coupled to the rear face of the liquid pumping system housing 18 if the application requires the liquid pumping system 16 to be mounted remotely on a metal surface. In exemplary embodiments of the invention, the liquid pumping system housing 18 circular mounting magnet 14 and the component mounting fixture 12 circular mounting magnets 14 may be thirty-two millimeters (32 mm) in diameter. In some embodiments, the component mounting fixture 12 may be fastened to a non-metallic surface as the liquid pumping system 16 may not be located in the direct vicinity of the evaporator 900, or the liquid pumping system 16 may be located, as an example, on a shelf. If an installation location is required utilizing wall anchors 88 with machine screws 90, the design of the component mounting fixture 12 is such that four (4) access through-holes for a Phillips-type screwdriver 92 are provided on the front face surface of the component mounting fixture 12 which align orthogonally with through-holes on the rear face of the component mounting fixture 12 for the wall anchor 88 machine screws 90, allowing the Phillips-type screwdriver 92 to be inserted into the front face through-holes to reach to the rear mounting face to secure the machine screws 90 into the wall anchors 88. A paper hole pattern template will be made available for expeditious marking and leveling of the four (4) wall anchor 88 locations.

In use, the liquid pumping system 16, optional battery pack 52 and the drain sanitizer solution reservoir 74 may be fitted to the component mounting fixture 12 which may be mounted adjacent to the evaporator 900. As non-limiting examples, the component mounting fixture 12 may be mounted to the evaporator 900 using a plurality of circular mounting magnets 14. The battery pack DC power cable 64 or the AC to DC power converter power cable 72 may plug into the DC power connector 50 of the liquid pumping system housing 18. The drain sanitizer solution 84 may be placed into the drain sanitizer solution reservoir 74, the drain sanitizer solution reservoir 74 being physically located in the drain sanitizer solution reservoir holding section 82 of the component mounting fixture 12. One (1) end of the intake tubing 24 may be coupled to the intake tubing coupler 26 and the other end of the intake tubing 24 may be placed into the drain sanitizer solution reservoir 74 via fluid communication with the drain sanitizer solution reservoir tubing coupler 80. One (1) end of the discharge tubing 30 may be coupled to the discharge tubing coupler 32 and the other end of the discharge tubing 30 may be placed into a location within the condensate collection and removal drain system 904. Routing of the discharge tubing 30 is assisted with the usage of discharge tube holders 950 (supplied). The discharge tubing 30 is inserted into the top opening slot of the discharge tube holder 950 which are then coupled to the evaporator 900 cabinet via a magnet 952. The usage of the magnetic tubing holders 952 prevent the discharge tubing 30 from being inadvertently squeezed closed with a conventional type of securing device similar to a plastic wire-tie which could potentially crush the soft silicone tubing cutting off the liquid flow. The usage of the magnetic tubing holders 952 also provides for an aesthetically appealing system installation.

The user may, if desired, select operational parameters such as the quantity to dispense and the dispensing interval frequency using the momentary pushbutton switch 46. The user may, if desired, manually activate the pump via the pump controller circuit board 34 by continuously pressing the momentary pushbutton switch 46. The pump controller circuit board 34 may periodically pump the drain sanitizer solution 84 automatically with no operator intervention, from the drain sanitizer solution reservoir 74 into the condensate collection and removal drain system 904 to prevent the growth of the microorganisms throughout the entire condensate collection and removal drain system 904 pathway.

The condensate drain line 906 may be operable to drain condensation from an evaporator condensate collection drain pan 902 but may be subject to a microorganism created blockage anywhere along the condensate drain line 906 pathway. Dispensing the drain sanitizer solution 84 into the condensate collection and removal drain system 904 may kill the microorganisms and prevent clogging. The optimum location to dispense a drain sanitizer solution 84 is directly into the evaporator condensate collection drain pan 902 as the evaporator condensate collection drain pan 902 is the originating location of the condensate generated by the evaporator 900. However, dispensing directly into the evaporator condensate collection drain pan 902 may not be readily accessible without tools depending on the design and physical construction of the condensate collection and removal drain system 904. The specifics of how the discharge tubing 30 is coupled into the condensate collection and removal drain system 904 will vary from installation to installation. While the drain sanitizer solution 84 may be dispensed through the discharge tubing 30 into multiple locations of opportunity within the condensate drain pathway, these potential dispense locations should be prioritized. A proper condensate collection and removal drain system 904 installation may contain all or some of the following components which ultimately affects selecting the optimum location to dispense into the condensate collection and removal drain system 904: a condensate drain line "P" trap 916, which prevents a backwards flow of air into the evaporator 900 by creating an air lock, which then facilitates the condensate flow out of the evaporator 900; a condensate drain line vent tube 908 which provides atmospheric venting to facilitate the unimpeded exit flow of the condensate through the condensate drain line 906; a condensate drain line access port 912 which provides a convenient location to vacuum out the condensate drain line 906 or add a drain sanitizer solution 84; a backup detection switch 926, which functions to turn off the air conditioning system due to a clogged and backed up condensate drain line 906; a secondary overflow drain pan 928 which may collect condensate overflows from the evaporator condensate collection drain pan 902. The need for a secondary overflow drain pan 928, if installed, is due to the propensity of bacterial generated blockages causing the primary evaporator condensate collection drain pan 902 to overflow. These condensate overflows are what the automatic air conditioner drain system sanitizer 10 is designed to permanently eliminate.

An evaporator condensate collection drain pan 902 will include a condensate drain pan outlet port 918 which is the evaporator condensate collection drain pan 902 condensate exit site. Typically, one (1) condensate drain pan outlet port 918 is required to fluidically couple the evaporator condensate collection drain pan 902 to the condensate drain line 906. A second port, if available, may typically be utilized to fluidically couple the evaporator condensate collection drain pan 902 to a backup detection switch 926. If there are any spare condensate drain pan outlet ports 918 available, these drain pan outlet port 918 may be closed-off with a condensate drain pan outlet port plug 920, or some type of sealing cover. Typical evaporator 900 systems may be installed horizontally or vertically which requires condensate drain pan outlet ports 918 available for both installation orientations, which may therefore provide at least one spare condensate drain pan outlet ports 918. In prioritizing the drain sanitizer solution 84 dispensing location, if available, a spare condensate drain pan outlet port 918 is the prioritized site for the connection of the liquid pumping system 16 discharge tubing 30.

Figure 22A:
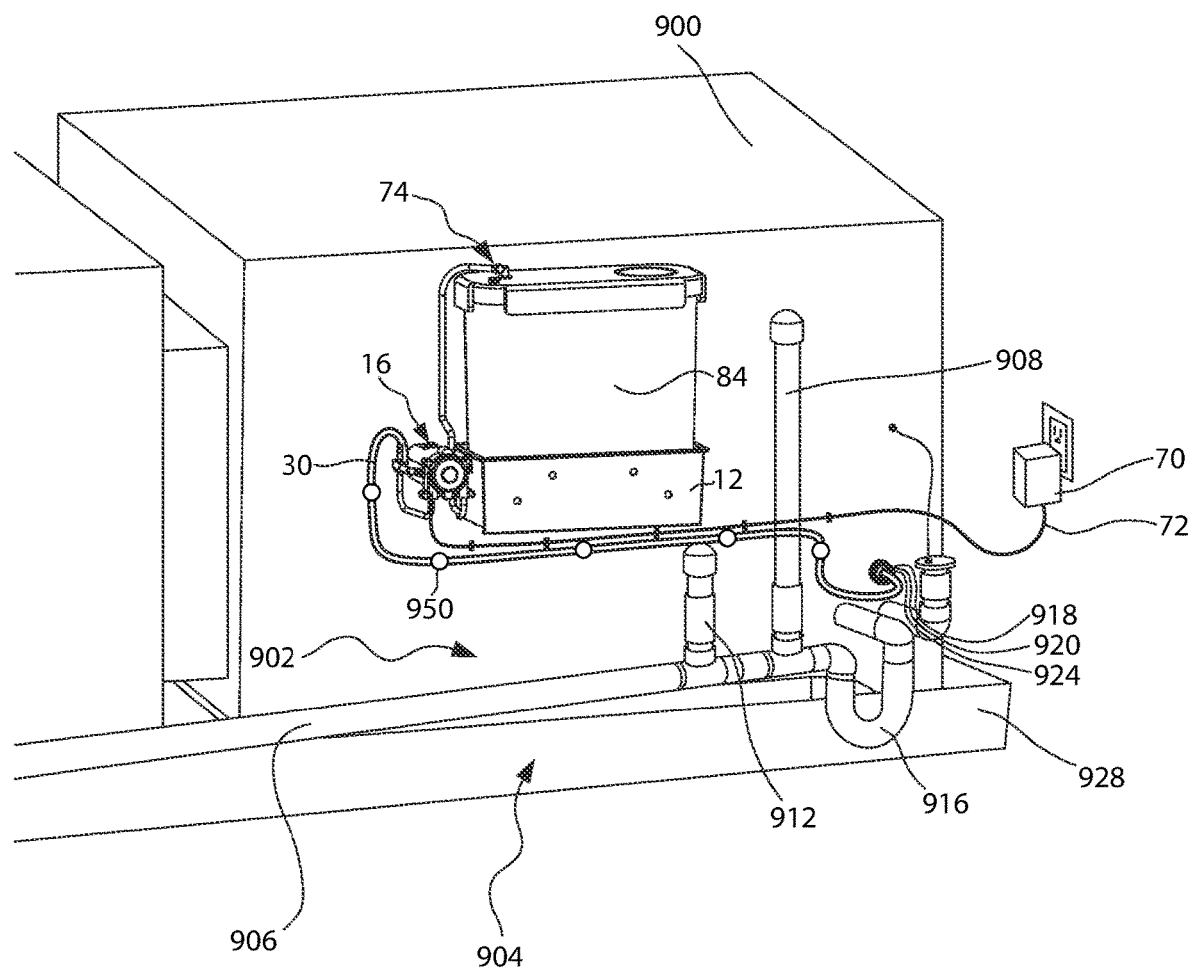
FIG. 22*a* is an in-use isometric view of an automatic air conditioner drain system sanitizer 10, according to a method of use of the present invention, illustrating the routing of the discharge tubing 30 which carries the drain sanitizer solution 84 into an evaporator condensate drain pan outlet port 918; power is shown supplied by an AC to DC power converter 70.

Non-limiting discharge tubing 30 routing examples may comprise and not be limited to, one (1) of these four (4) options:

See FIG. 22a. Routing the discharge tubing 30 into the bottom of the evaporator condensate collection drain pan 902 via an available condensate drain pan outlet port 918. The discharge tubing 30 is coupled to a pass-through bulkhead tubing coupler 924 (supplied) which has been fitted to a condensate drain pan outlet port plug 920, which comprises a sealing O-ring 922. This dispensing method is the preferred method for connecting the discharge tubing 30 to the condensate collection and removal drain system 904, as the evaporator condensate collection drain pan 902 is the originating location of the condensate generated by the evaporator 900 and will subsequently provide the maximum level of bacterial sanitizing throughout the entire condensate collection and removal drain system 904 pathway.

Figure 22B:
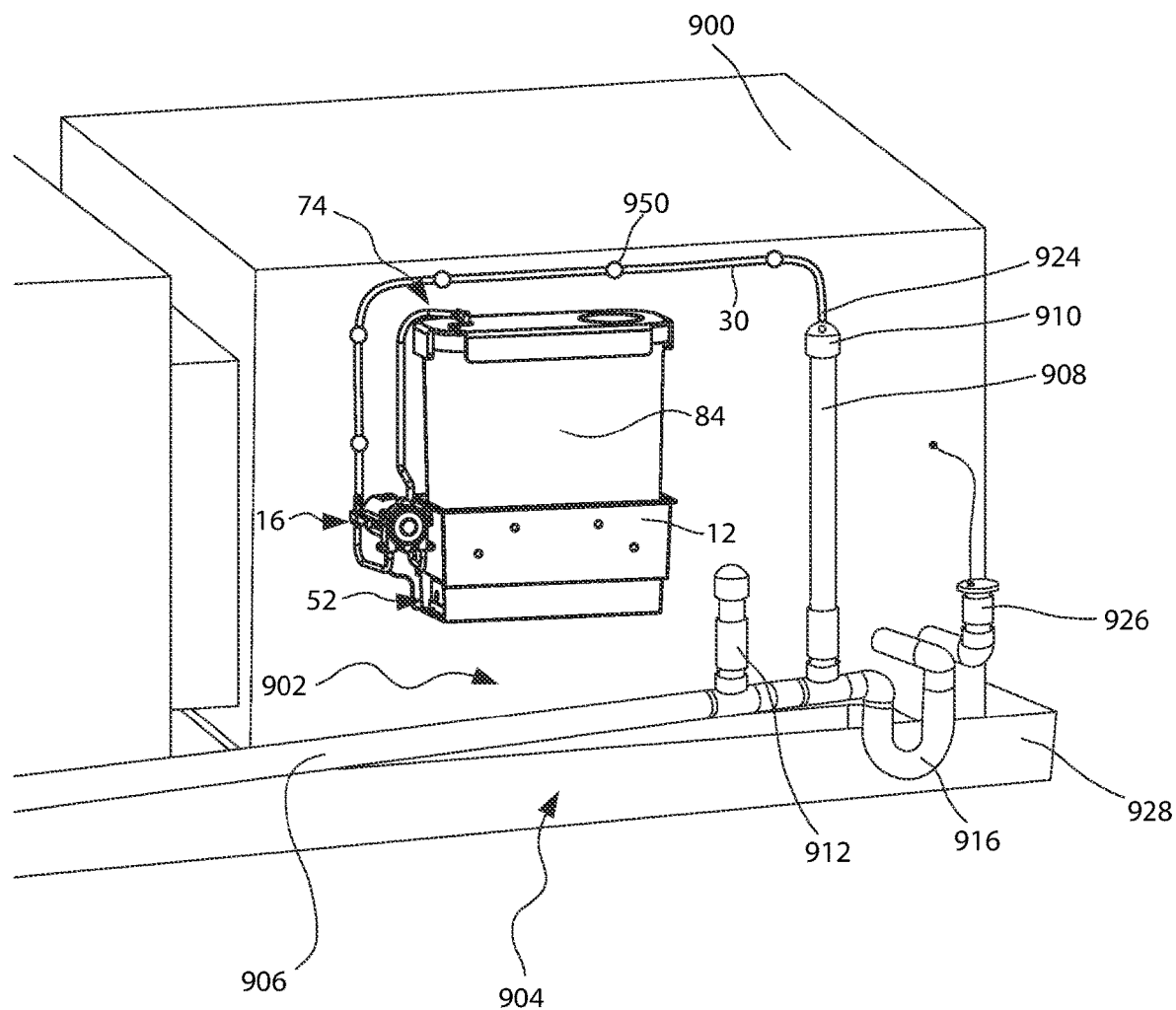
FIG. 22*b* is an in-use isometric view of an automatic air conditioner drain system sanitizer 10, according to a method of use of the present invention, illustrating the routing of the discharge tubing 30 which carries the drain sanitizer solution 84 into the condensate drain line vent tube 908 utilizing a condensate drain line vent tube cap 910 which has been fitted with a pass-through bulkhead tubing coupler 924 and an aperture for venting; power is shown supplied by an optional battery pack 52.

See FIG. 22b. Routing the discharge tubing 30 into the condensate drain line 906 via a condensate drain line vent tube 908. The condensate drain line vent tube 908 may or may not be capped. If capped, there must be an aperture in the cap to allow air to flow into the condensate drain line vent tube 908. A modified condensate drain line vent tube cap 901 (supplied) is installed which has been fitted with a pass-through bulkhead tubing coupler 924 and a venting aperture.

Figure 22C:
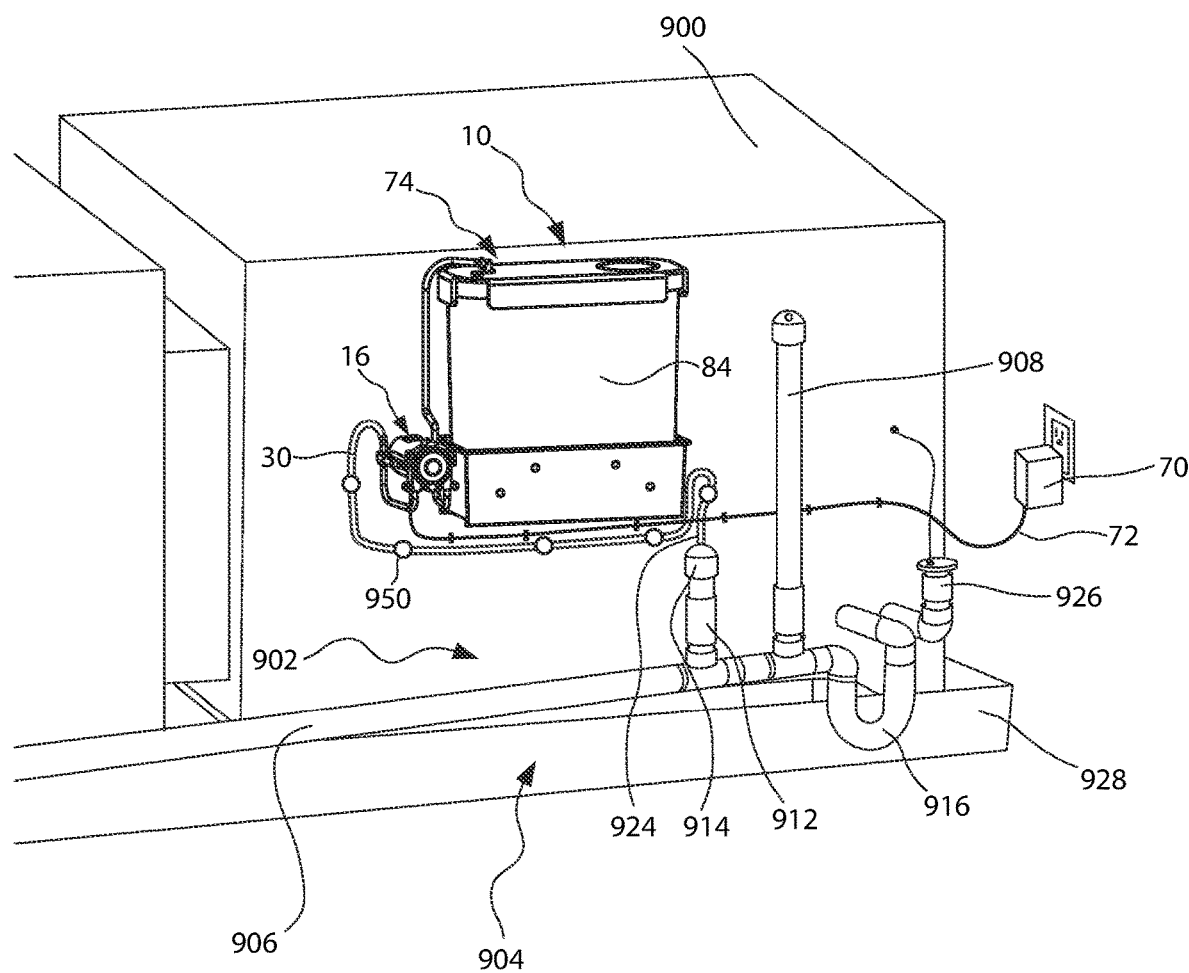
FIG. 22*c* is an in-use isometric view of an automatic air conditioner drain system sanitizer 10, according to a method of use of the present invention, illustrating the routing of the discharge tubing 30 which carries the drain sanitizer solution 84 into the condensate drain line access port 912 utilizing a condensate drain line access port cap 914 which has been fitted with a pass-through bulkhead tubing coupler 924; power is shown supplied by an AC to DC power converter 70.

See FIG. 22c. Routing the discharge tubing 30 into the condensate drain line 906 via a condensate drain line access port 912. The condensate drain line access port 912 tube should be capped closed and will not have an aperture. A modified condensate drain line access port cap 914 (supplied) is installed which has been fitted with a pass-through bulkhead tubing coupler 924.

Figure 22D:
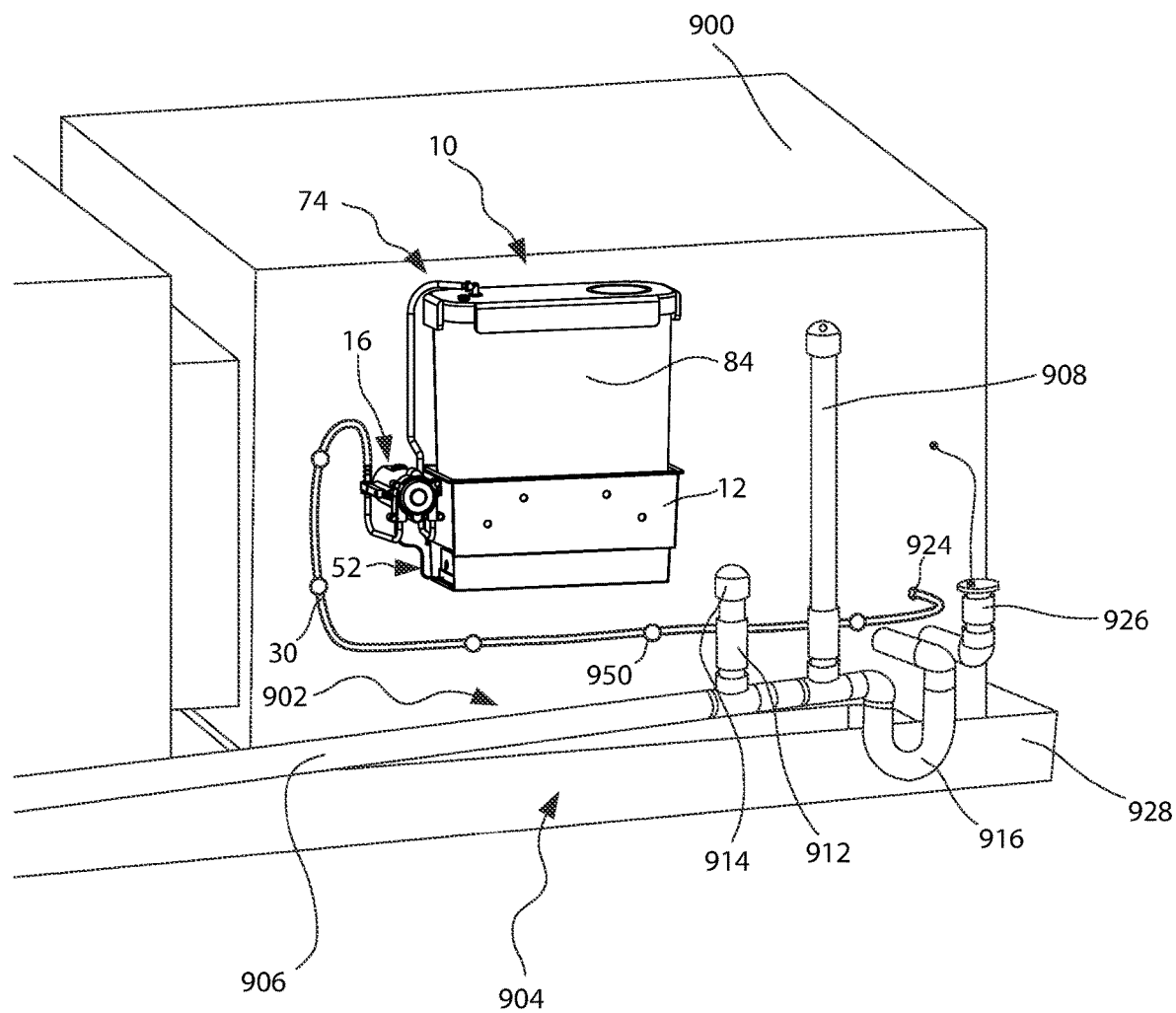
FIG. 22*d* is an in-use isometric view of an automatic air conditioner drain system sanitizer 10, according to a method of use of the present invention, illustrating the routing of the discharge tubing 30 which carries the drain sanitizer solution 84 into an aperture which has been manually opened into the evaporator cabinet and the cabinet fitted with a pass-through bulkhead tubing coupler 924; power is shown supplied by the optional battery pack 52.
Figure 22E:
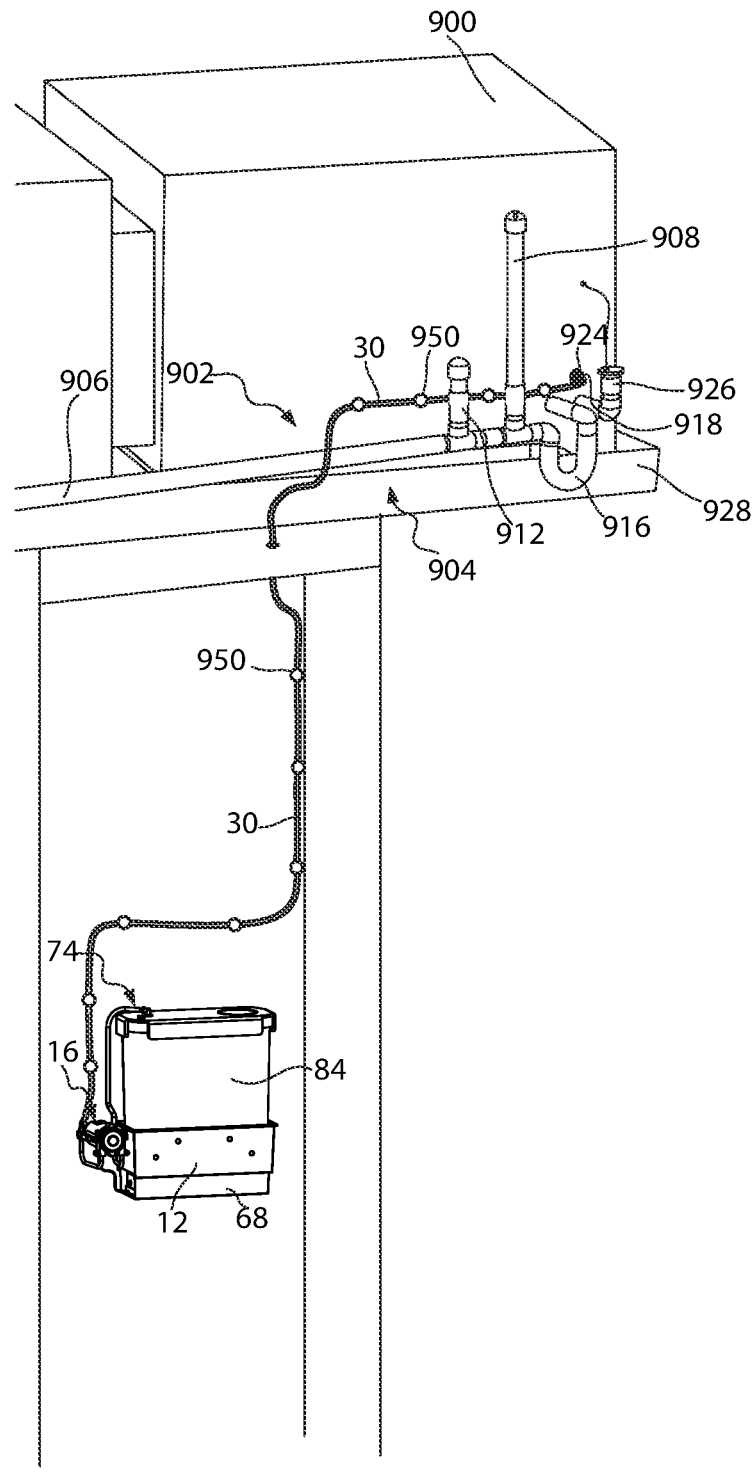
FIG. 22*e* is an in-use view of an automatic air conditioner drain system sanitizer 10, according to a method of use of the present invention, illustrating an example of an attic air conditioner installation with the automatic air conditioner drain system sanitizer 10 installed on the floor below; power is shown supplied by an optional battery pack 52.

See FIG. 22d. Routing the discharge tubing 30 into the bottom of the evaporator condensate collection drain pan 902 via an aperture manually added into the air conditioner cabinet. The aperture will be fitted with a pass-through bulkhead tubing coupler 924 (supplied) which will allow the drain sanitizer solution 84 to be directly injected in the evaporator condensate collection drain pan 902. This is the second highest prioritized method for connecting the discharge tubing 30 to the condensate collection and removal drain system 904. This installation method will require more effort and skill as this method will require manually creating an aperture in the evaporator 900 housing.

The automatic air conditioner drain system sanitizer 10 package provides the necessary fittings to facilitate injecting the drain sanitizer solution 84 directly into the evaporator condensate collection drain pan 902 which may be as simple as replacing a spare condensate drain pan outlet port plug 920. However, based on myriad condensate collection and removal drain system 904 physical installation variations, unrestricted access to the evaporator condensate collection drain pan 902 may not be available. If this is the case, there are multiple alternative locations to dispense the sanitizing drain sanitizer solution 84 which provides bacterial elimination to the remainder of the condensate drain line 906 pathway. According to accepted industry practices for maintenance of the condensate drain line 906, monthly dispensing of a drain sanitizer solution 84 into the condensate drain line 906 downstream of the evaporator condensate collection drain pan 902 is the informally accepted standard practice across the industry. If injecting directly into the evaporator condensate collection drain pan 902 is not possible, on a minimum yearly basis, the evaporator 900 housing access panel should be removed and the evaporator condensate collection drain pan 902 inspected and cleaned as the evaporator condensate collection drain pan 902 will be upstream of the dispensing location.

Figure 24A:
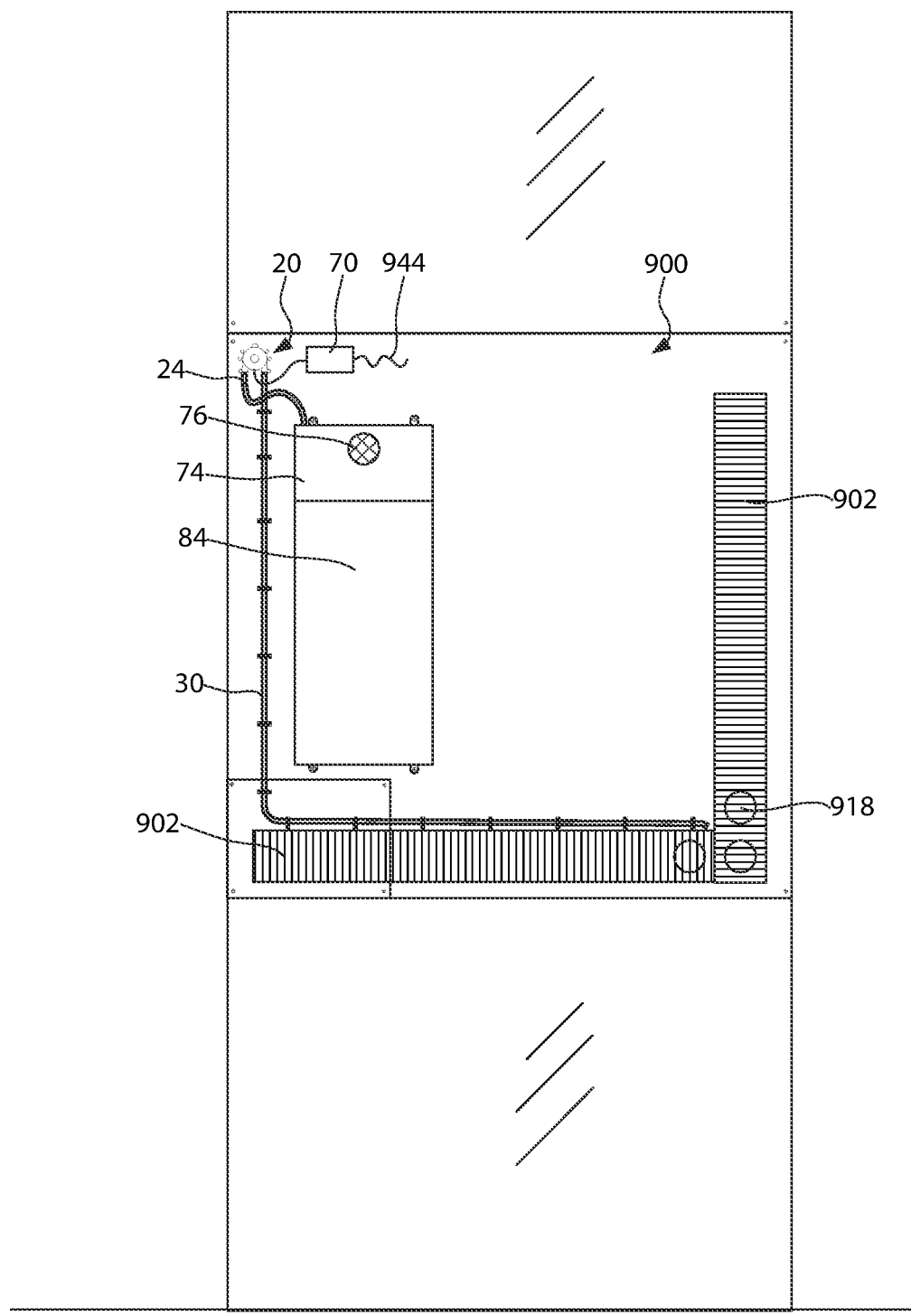
FIG. 24*a* is an in-use orthogonal front view of an automatic air conditioner drain system sanitizer 10, according to a method of use of the present invention, illustrating a conceptual example of the automatic air conditioner drain system sanitizer 10 installed in an Original Equipment Manufacturer (OEM) product at the factory; the front access panel is shown opened; and, FIG. 24*b* is an in-use orthogonal front view of an automatic air conditioner drain system sanitizer 10, according to a method of use of the present invention, illustrating a conceptual example of the automatic air conditioner drain system sanitizer 10 installed in an Original Equipment Manufacturer (OEM) product at the factory; the front access panel is shown closed.
Figure 24B:
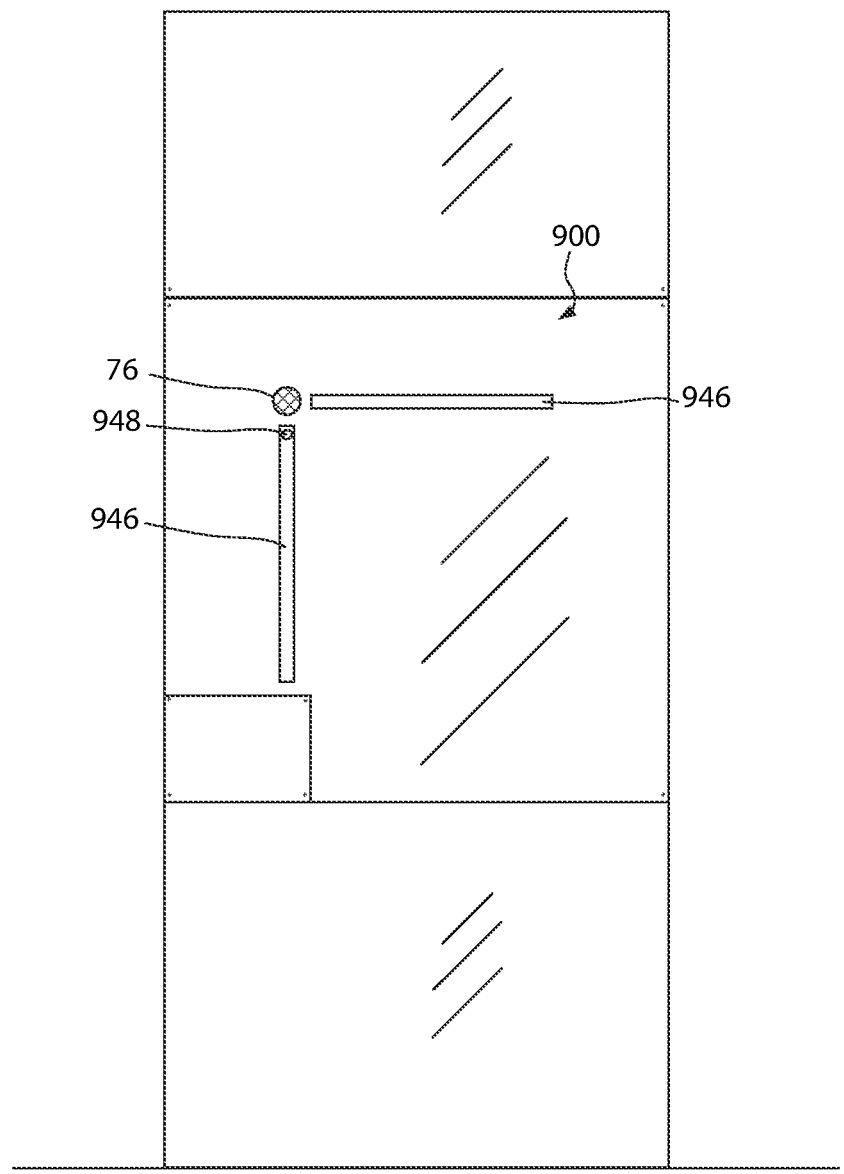

In a preferred embodiment to eliminate the bacteria accumulation in a condensate collection and removal drain system 904 at the condensate origination site, the optimum solution is an Original Equipment Manufacturer (OEM) installed solution. FIGS. 24a and 24b are an example of a concept for an "Air Conditioner Self-Cleaning Drain System" which integrates the automatic air conditioner drain system sanitizer 10 directly into the evaporator 900 cabinet. The liquid pumping system 16 and the drain sanitizer solution reservoir 74 would be factory installed internally to the evaporator 900 housing, the drain sanitizer solution reservoir 74 having an drain sanitizer solution reservoir lid 76 external to the evaporator 900 housing to allow for external refilling. Power may be derived from the main electrical cable 944 powering the air conditioner via an AC to DC converter. The drain sanitizer solution reservoir 74 may be designed to accommodate horizontal or vertical fitting of the evaporator 900 housing. A see-through observation window 946 may provide visual access to the reservoir level in both horizontal or vertical installation of the evaporator 900 housing, and a health status LED indicator 948 may be provided. The automatic air conditioner drain system sanitizer 10 would be configured for proper orientation at the time of installation.

The exact specifications, materials used and method of use of the automatic air conditioner drain system sanitizer 10 may vary upon manufacturing. The foregoing descriptions of specific embodiments of the automatic air conditioner drain system sanitizer 10 have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated.

What is claimed is:

1. An automatic air conditioner drain system sanitizer, comprising:
　　a pump moving a plurality of drain sanitizer solution from a pump inlet to a pump outlet automatically;
　　a solution reservoir containing a drain sanitizer solution; the solution reservoir includes a solution reservoir lid, an atmospheric equalization vent, and a solution reservoir tubing coupler; the pump draws the drain sanitizer solution into the pump from the solution reservoir;
　　a pump controller circuit board which operates the pump;
　　a wireless communications circuit board which provides control, settings adjustments, system dispensing history data and system overall health status;
　　an operator interface momentary pushbutton switch which enables a plurality of utilities including manual continuous pump activation control, selection of pre-set quantity pump dispense controls, incoming power level indication, dispense interval frequency selection control and dispense quantity timing selection control.

2. The automatic air conditioner drain system sanitizer, according to claim 1, wherein the pump is an electromechanical pump.

3. The automatic air conditioner drain system sanitizer, according to claim 1, wherein the pump is a peristaltic pump.

4. The automatic air conditioner drain system sanitizer, according to claim 1, wherein the pump moves the drain sanitizer solution by applying a rotary motion, a reciprocating motion, a linear motion, or a combination thereof by one or more gears, one or more screws, one or more pistons, one or more rollers, one or more shuttle blocks, one or more vanes, one or more diaphragms, one or more plungers, one or more impellers or combinations thereof.

5. The automatic air conditioner drain system sanitizer, according to claim 1, wherein the pump draws the drain sanitizer solution into the pump from the solution reservoir through a plurality of intake tubing that is coupled via fluid communication to the pump inlet via an intake tubing coupler.

6. The automatic air conditioner drain system sanitizer, according to claim 1, wherein the pump discharges the drain sanitizer solution through a plurality of discharge tubing that is coupled via fluid communication to the pump outlet via a discharge tubing coupler.

7. The automatic air conditioner drain system sanitizer, according to claim 6, wherein the drain sanitizer solution is dispensed through the discharge tubing into a condensate collection and removal drain system.

8. The automatic air conditioner drain system sanitizer, according to claim 6, wherein the drain line is operable to drain a plurality of condensation from an evaporator.

9. The automatic air conditioner drain system sanitizer, according to claim 6, wherein the drain sanitizer solution kills a plurality of microorganisms in a condensate collection and removal drain system pathway to prevent clogging.

10. The automatic air conditioner drain system sanitizer, according to claim 6, wherein the discharge tubing is routed into a bottom of an evaporator via an accessory drain port plug which is fitted with a pass-through bulkhead tubing coupler.

11. The automatic air conditioner drain system sanitizer, according to claim 6, wherein the discharge tubing is routed into a bottom of a evaporator via a pass-through bulkhead tubing coupler fitted to an added aperture in the evaporator housing access panel.

12. The automatic air conditioner drain system sanitizer, according to claim 6, wherein the discharge tubing is routed directly into the drain line via a condensate drain line vent tube.

13. The automatic air conditioner drain system sanitizer, according to claim 6, wherein the discharge tubing is routed into a drain line via a condensate drain line access port that is closed with a cap.

14. The automatic air conditioner drain system sanitizer, according to claim 12, wherein a cap is replaced with a different cap which is fitted with a pass-through bulkhead tubing coupler and a venting aperture.

15. The automatic air conditioner drain system sanitizer, according to claim 13, wherein the cap is replaced with a different cap which is fitted with a pass-through bulkhead tubing coupler.

16. The automatic air conditioner drain system sanitizer, according to claim 10, wherein the discharge tubing is routed into a drain pan under an evaporator which is coupled via fluid communication to a drain line.

17. The automatic air conditioner drain system sanitizer, according to claim 1, wherein the controller is a microcontroller having a computer processor that includes a central processing unit having one or more integrated circuits that determines when to dispense the drain sanitizer solution, when to energize the pump, which direction to rotate the pump, when to control the drain sanitizer solution dispensed and when to deenergize a motor.

18. The automatic air conditioner drain system sanitizer, according to claim 1, wherein the controller receives one or more inputs from an internal timer and controls one or more outputs coupled to a motor drive circuit and wherein the controller includes a battery pack containing one or more batteries.

19. The automatic air conditioner drain system sanitizer, according to claim 17, wherein a timer counts a plurality of clock ticks in order to track elapsed time and a plurality of circular mounting magnets are coupled to a rear face of a component mounting fixture;
 wherein the component mounting fixture efficiently organizes the mounting of the sanitizing solution reservoir, liquid pumping system and an optional battery pack; and,
 wherein the liquid pumping system housing may include a single circular mounting magnet coupled to the rear face of the housing.

20. The automatic air conditioner drain system sanitizer, according to claim 1, further comprising a liquid pumping system housing which incorporates the pump controller circuit board, wireless communication circuit board, dispensing pump, input DC power connector and a pushbutton switch with a LED indicator light.

* * * * *